US007928243B2

(12) United States Patent
Gu et al.

(10) Patent No.: US 7,928,243 B2
(45) Date of Patent: Apr. 19, 2011

(54) ACETYL-COA CARBOXYLASE (ACC) INHIBITORS AND THEIR USE IN DIABETES, OBESITY AND METABOLIC SYNDROME

(75) Inventors: Yu Gui Gu, Libertyville, IL (US); Richard F. Clark, Gurnee, IL (US); Qun Li, Lbertyville, IL (US); Moshe Weitzberg, Highland Park, IL (US); Hing Sham, South San Francisco, CA (US)

(73) Assignee: Abbott Laboratories, Abbott Park, IL (US)

( * ) Notice: Subject to any disclaimer, the term of this patent is extended or adjusted under 35 U.S.C. 154(b) by 495 days.

(21) Appl. No.: 11/950,692

(22) Filed: Dec. 5, 2007

(65) Prior Publication Data

US 2008/0161368 A1 Jul. 3, 2008

Related U.S. Application Data

(60) Provisional application No. 60/871,304, filed on Dec. 21, 2006.

(51) Int. Cl.
*A61K 31/426* (2006.01)
*C07D 277/34* (2006.01)
(52) U.S. Cl. ........................................ 548/186; 514/369
(58) Field of Classification Search ................... 548/186
See application file for complete search history.

(56) References Cited

U.S. PATENT DOCUMENTS

2006/0178400 A1  8/2006  Beutel et al.

FOREIGN PATENT DOCUMENTS

WO   WO-02/083643 A1 * 10/2002

OTHER PUBLICATIONS

Abu-Elheiga, et al., J. Biol. Chem. 272:10669-10677 (1997).
Abu-Elheiga, et al., Proc. Natl. Acad. Sci. 100:10207-10212 (2003).
Abu-Elheiga, et al., Proc. Natl. Acad. Sci. 97:1444-1449 (2000).
Abu-Elheiga, et al., Science 291:2613-2616 (2001).
Clark, et al., Bioorganic & Med. Chem. Letters 16(23): 6078-6081 (2006).
Greene, et al., Protecting Groups in Chemical Synthesis (3$^{rd}$ ed.), John Wiley & Sons, NY (1999) Table of Contents.
Gu, et al., Journal of Med. Chem. 49(13): 3770-3773 (2006).
Higuchi, et al., Pro-drugs as Novel Delivery Systems, vol. 14 of the A.C.S. Symposium Series (1975) Table of Contents.
Hulver, et al., Am. Journal Physiol. Endrocrinol. Metab. 284:E741-E747 (2003).
Mao, et al., Proc. Natl. Acad. Sci. 100:7515-7520 (2003).
Roche, ed., Bioreversible Carriers in Drug Design, American Pharmaceutical Association and Pergamon Press (1987) Table of Contents.
Ruderman, et al., Nat. Rev. Drug Discov. 3:340-351 (2004).
Sinha, et al., Diabetes 51:1022-1027 (2002).
Steyn, et al., Public Health Nutr. 7:147-165 (2004).
Turkoglu, et al., Obes. Surg. 13:699-705 (2003).
Yamauchi, et al., Nat. Med. 7:941-946 (2001).

* cited by examiner

*Primary Examiner* — Laura L. Stockton
(74) *Attorney, Agent, or Firm* — Sreenivasarao Vepachedu; Andrew M. Parial

(57) ABSTRACT

The present invention relates to compounds of formula (I):

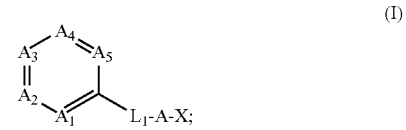

Pharmaceutical compositions and methods that are useful in the treatment or prevention of metabolic diseases or conditions are also provided.

11 Claims, No Drawings

ACETYL-COA CARBOXYLASE (ACC) INHIBITORS AND THEIR USE IN DIABETES, OBESITY AND METABOLIC SYNDROME

CROSS-REFERENCE SECTION TO RELATED APPLICATIONS

This application claims priority to U.S. application Ser. No. 60/871,304, filed Dec. 21, 2006, and is incorporated herein by reference in its entirety.

FIELD OF THE INVENTION

The present invention relates to compounds, pharmaceutical compositions, and related methods for the treatment or prevention of various diseases such as diabetes, obesity, and metabolic syndrome.

BACKGROUND OF THE INVENTION

The incidence of type 2 diabetes has dramatically increased over the past decade. This epidemic is largely attributed to proliferation of key risk factors, which include a sedentary lifestyle, a high fat diet, obesity and the demographic shift to a more aged population. There is ample evidence to indicate that increased abdominal obesity and physical inactivity contribute significantly to the development of type 2 diabetes (Turkoglu C, Duman B S, Gunay D, Cagatay P, Ozcan R, Buyukdevrim A S: Effect of abdominal obesity on insulin resistance and the components of the metabolic syndrome: evidence supporting obesity as the central feature. Obes Surg 2003; 13: 699-705. Steyn N P, Mann J, Bennett P H, Temple N, Zimmet P, Tuomilehto J, Lindstrom J, Louheranta A: Diet, nutrition and the prevention of type 2 diabetes. Public Health Nutr 2004; 7: 147-65).

At the cellular level, an increase in ectopic fat storage in nonadipose tissues such as in muscle, liver and pancreas is a strong predictor of the development of insulin resistance and type 2 diabetics (Hulver M W, Berggren J R, Cortright R N, Dudek R W, Thompson R P, Pories W J, MacDonald K G, Cline G W, Shulman G I, Dohm G I, Houmard J A: *Skeletal muscle lipid metabolism with obesity. Am J Physiol Endocrinol Metab* 2003; 284: E741-7. Sinha R, Dufour S, Petersen K F, LeBon V, Enoksson S, Ma Y Z, Savoye M, Rothman D L, Shulman G I, Caprio S: *Assessment of skeletal muscle triglyceride content by $^1H$ nuclear magnetic resonance spectroscopy in lean and obese adolescents: relationships to insulin sensitivity, total body fat, and central adiposity. Diabetes* 2002; 51: 1022-7). The precise mechanism of how increased intracellular lipid content exacerbates whole body insulin sensitivity is unclear at present, but it has been postulated that increased long chain fatty acyl-CoAs, ceramide or diacylglycerol, whose contents are proportional to the accumulation of intramyocellular triglyceride, antagonizes metabolic actions of insulin, reduces muscle glucose uptake and inhibits hepatic glucose production (Sinha R, Dufour S, Petersen K F, LeBon V, Enoksson S, Ma Y Z, Savoye M, Rothman D L, Shulman G I, Caprio S: *Assessment of skeletal muscle triglyceride content by $^1H$ nuclear magnetic resonance spectroscopy in lean and obese adolescents: relationships to insulin sensitivity, total body fat, and central adiposity. Diabetes* 2002; 51: 1022-7. Friedman J: *Fat in all the wrong places. Nature* 2002; 415: 268-9). As muscle is the primary site of metabolic action of insulin, the development of muscle insulin resistance along with liver insulin resistance are thus inherently linked to the development of whole body insulin resistance.

In order to increase muscle and liver fat oxidation and thus limit the concentration of LCFACoA's we aim to inhibit the activity of Acetyl CoA Carboxylase (ACC), which catalyzes the production of malonyl-CoA from acetyl-CoA. Malonyl-CoA is an intermediate substrate that plays an important role in the overall fatty acid metabolism: Malonyl-CoA is utilized by fatty acid synthase for de novo lipogenesis, and also acts as a potent allosteric inhibitor of carnitine palmitoyltransferase 1 (CPT1), a mitochondrial membrane protein that shuttles long chain fatty acyl CoAs into the mitochondrial where they are oxidized (Ruderman N, Prentki M: *AMP kinase and malonyl-CoA: targets for therapy of the metabolic syndrome. Nat Rev Drug Discov* 2004; 3: 340-51). A small molecule inhibitor of ACC would thus limit de novo lipid synthesis, de-inhibit CPT1 and subsequently increase fat oxidation.

In rodents and in humans, there are two known isoforms of ACC that are encoded by distinct genes and share approximately 70% amino acids identity. ACC1, which encodes a 265 KD protein, is highly expressed in the cytosol of lipogenic tissues such as liver and adipose, whereas 280 KD ACC2 protein is preferentially expressed in oxidative tissues, skeletal muscle and heart (Mao J, Chirala S S, Wakil S J: *Human acetyl-CoA carboxylase 1 gene: presence of three promoters and heterogeneity at the 5'-untranslated mRNA region. Proc Natl Acad Sci USA* 2003, 100: 7515-20. Abu-Elheiga L, Almarza-Ortega D B, Baldini A, Wakil S J: *Human acetyl-CoA carboxylase 2. Molecular cloning, characterization, chromosomal mapping, and evidence for two isoforms. J Biol Chem* 1997, 272: 10669-77). ACC2 has a unique 114 amino acid N-terminus with a putative transmembrane domain (TM), which is thought to be responsible for mitochondrial targeting (Abu-Elheiga L, Brinkley W R, Zhong L, Chirala S S, Woldegiorgis G, Wakil S J: *The subcellular localization of acetyl-CoA carboxylase 2. Proc Natl Acad Sci USA* 2000; 97: 1444-9). Based on tissue distribution and subcellular localization of these two isoforms, the current hypothesis is that a distinct pool of Malonyl-CoA produced from a pathway catalysed by ACC1 is preferentially converted into fatty acids by fatty acid synthase, whereas another pool of Malonyl-CoA synthesized primarily from reactions catalysed by ACC2, presumed localized in near mitochondria, can be involved in the inhibition of CPT1 (Abu-Elheiga L, Brinkley W R, Zhong L, Chirala S S, Woldegiorgis G, Wakil S J: *The subcellular localization of acetyl-CoA carboxylase 2. Proc Natl Acad Sci USA* 2000; 97: 1444-9). Therefore, ACC1 inhibition reduces fatty acid synthesis and can be beneficial for use in treating diseases such as metabolic syndrome.

Genetic studies have demonstrated that ACC2 knockout mice are healthy and fertile with a favorable metabolic phenotype, increased fatty acid oxidation, increased thermogenesis, reduced hepatic TG content and subsequent decrease in body weight despite increase in food intake compared to their littermates (Abu-Elheiga L, Matzuk M M, Abo-Hashema K A, Wakil S J: *Continuous fatty acid oxidation and reduced fat storage in mice lacking acetyl-CoA carboxylase 2. Science* 2001; 291: 2613-6). In addition, these mice are resistant against high fat diet-induced obesity and insulin resistance (Abu-Elheiga L, Oh W, Kordari P, Wakil S J. *Acetyl-CoA carboxylase 2 mutant mice are protected against obesity and diabetes induced by high-fat/high-carbohydrate diets. Proc Natl Acad Sci USA* 2003; 100: 10207-12). Also, recently it was demonstrated that the effects of leptin and adiponectin, cytokines secreted from adipose tissue, to increase fatty acid oxidation are at least due in part to the inhibition of ACC in liver and skeletal muscle (Yamauchi T, Kamon J, Waki H, Terauchi Y, Kubota N, Hara K, Mori Y, Ide T, Murakami K, Tsuboyama-Kasaoka N, Ezaki O, Akanuma Y, Gavrilova O, Vinson C, Reitman M L, Kagechika H, Shudo K, Yoda M, Nakano Y, Tobe K, Nagai R, Kimura S, Tomita M, Froguel P, Kadowaki T: *The fat-derived hormone adiponectin reverses insulin resistance associated with both lipoatrophy and obesity.* Nat Med 2001; 7: 941-6). Taken together, these data support that the discovery that small molecular inhibitors of ACC2 can provide a favorable metabolic profile against obesity induced type 2 diabetic patients. Furthermore, the dual inhibition of ACC1 and ACC2 can provide the profile needed to demonstrate benefit for patients exhibiting conditions of metabolic syndrome.

SUMMARY OF THE INVENTION

One aspect of the invention is directed to compounds of formula (I), or a pharmaceutical acceptable salt, prodrug, salt of a prodrug, or a combination thereof;

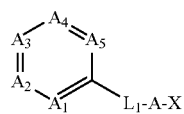

(I)

wherein $A_1$, $A_4$ and $A_5$ are each independently N or $C(R^1)$;

one of $A_2$ and $A_3$ is $C(-L_2-R^2)$ and the other is N or $C(R^1)$; provided that no more than two of $A_1, A_2, A_3, A_4$ and $A_5$ are N;

$R^1$ at each occurrence is independently hydrogen, alkyl, halogen or haloalkyl;

$R^2$ is alkyl, aryl or heteroaryl; wherein the aryl and heteroaryl are independently unsubstituted or substituted with 1, 2, 3, 4 or 5 substituents selected from the group consisting of —CN, —NO$_2$, alkyl, haloalkyl, —O(R$_a$), —S(R$_a$), —S(O)R$_a$, —S(O)$_2$R$_a$, —NR$_a$R$_b$, —OC(O)R$_a$, —N(R$_b$)C(O)R$_a$, —N(R$_b$)S(O)$_2$R$_a$, —N(R$_b$)C(O)OR$_a$, —N(R$_b$)C(O)NR$_a$R$_b$, —N(R$_b$)S(O)$_2$NR$_a$R$_b$, —C(O)R$_a$, —C(O)OR$_a$—C(O) NR$_a$R$_b$, —S(O)$_2$NR$_a$R$_b$, —(CR$^y$R$^z$)$_n$—CN, —(CR$^y$R$^z$)$_n$—NO$_2$, —(CR$^y$R$^z$)$_n$—O(R$_a$), —(CR$^y$R$^z$)$_n$—S(R$_a$), —(CR$^y$R$^z$)$_n$—S(O)R$_a$, —(CR$^y$R$^z$)$_n$—S(O)$_2$R$_a$, —(CR$^y$R$^z$)$_n$—NR$_a$R$_b$, —(CR$^y$R$^z$)$_n$—OC(O)R$_a$, —(CR$^y$R$^z$)$_n$—N(R$_b$)C(O)R$_a$, —(CR$^y$R$^z$)$_n$—N(R$_b$)S(O)$_2$R$_a$, —(CR$^y$R$^z$)$_n$—N(R$_b$)C(O) OR$_a$, —(CR$^y$R$^z$)$_n$—N(R$_b$)C(O)NR$_a$R$_b$, —(CR$^y$R$^z$)$_n$—N(R$_b$) S(O)$_2$NR$_a$R$_b$, —(CR$^y$R$^z$)$_n$—C(O)R$_a$, —(CR$^y$R$^z$)$_n$—C(O) OR$_a$, —(CR$^y$R$^z$)$_n$—C(O)NR$_a$R$_b$, and —(CR$^y$R$^z$)$_n$—S(O)$_2$ NR$_a$R$_b$;

$L_1$ is O, N(R$^x$), S, S(O), S(O)$_2$, or C(R$^y$R$^z$)$_m$;

$L_2$ is O, N(R$^x$), S, S(O), S(O)$_2$, or C(R$^y$R$^z$)$_m$;

$R^x$ at each occurrence is independently hydrogen, alkyl or haloalkyl;

m and n at each occurrence are independently 1, 2 or 3;

$R_a$ at each occurrence is independently hydrogen, alkyl, alkenyl, haloalkyl, aryl, heteroaryl, arylalkyl or heteroarylalkyl, $R_a$, at each occurrence is independently alkyl, alkenyl, haloalkyl, aryl, heteroaryl, arylalkyl or heteroarylalkyl.

$R_b$ at each occurrence is independently hydrogen, alkyl, alkenyl or haloalkyl;

wherein the aryl, heteroaryl, aryl moiety of the arylalkyl and the heteroaryl moiety of the heteroarylalkyl as represented by $R_a$ and $R_a$, are independently unsubstituted or substituted with 1, 2, 3 or 4 substituents selected from the group consisting of alkyl, haloalkyl, alkenyl, hydroxy, alkoxy, —N(H)$_2$, —N(H)(alkyl), —N(alkyl)$_2$, —C(O)H, —C(O)alkyl, —C(O)OH, —C(O)O(alkyl), —C(O)NH$_2$, —C(O)N(H)(alkyl), —C(O)N(alkyl)$_2$, —CN and —NO$_2$, A is phenyl or monocyclic heteroaryl; A is connected to $L_1$ and X through the carbon atoms in the ring and is optionally further substituted with 1 or 2 substituents selected from the group consisting of alkyl, halogen, haloalkyl and hydroxyalkyl;

X is —C(H)=N—O—(CR$^y$R$^z$)$_p$—NR$_d$R$_e$, —O—(CR$^y$R$^z$)$_p$—NR$_d$R$_e$, —(CR$^y$R$^z$)$_q$—NR$_d$R$_e$, or —C(H)=C (H)—(CR$^y$R$^z$)$_q$—NR$_d$R$_e$;

$R^y$ and $R^z$ at each occurrence are independently hydrogen, alkyl, haloalkyl or hydroxyalkyl;

p at each occurrence is independently 2 or 3;

q at each occurrence is independently 1, 2 or 3;

$R_d$ at each occurrence is independently hydrogen, alkyl, haloalkyl, —C(O)(alkyl), —C(O)N(H)$_2$, —C(O)N(H)(alkyl) or —C(O)N(alkyl)$_2$; and $R_e$ at each occurrence is independently hydrogen, alkyl or haloalkyl.

Another aspect of the invention is directed to the pharmaceutical compositions including compounds disclosed herein. Such compositions can be administered in accordance with a method of the invention, typically for the treatment or prevention of conditions and disorders related to ACC. A further aspect of the invention relates to a method of inhibiting ACC activity. The method is useful for treating or preventing conditions and disorders related to ACC in mammals. More particularly, the method is useful for treating or preventing conditions and disorders related to metabolic syndrome, type II diabetes, obesity, atherosclerosis and cardiovascular diseases in mammals. Accordingly, the compounds and compositions disclosed herein are useful as a medicament for treating or preventing disease modulated by ACC. Furthermore, processes for making compounds disclosed herein are contemplated.

DETAILED DESCRIPTION OF THE INVENTION

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds, which can be isolated in a useful degree of purity from a reaction mixture.

Certain terms as used in the specification are intended to refer to the following definitions, as detailed below.

The term "alkenyl" as used herein means a straight or branched chain hydrocarbon including from 2 to 10 carbons and including at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means —O-alkyl.

The term "alkyl" as used herein means a straight or branched chain hydrocarbon including from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" as used herein means a diradical of a branched or straight saturated hydrocarbon chain, preferably having one to ten carbon atoms, preferably from one to six carbon atoms and more preferably from one to three carbon atoms. This term is exemplified by groups such as methylene (—CH$_2$—), ethylene (—CH$_2$—CH$_2$—), the propylene isomers (e.g. —CH$_2$—CH$_2$—CH$_2$— and —C(H)(CH$_3$)CH$_2$—), and the like.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. The phenyl and the bicyclic aryl groups of the present invention are unsubstituted or substituted. The bicyclic aryl is attached to the parent molecular moiety through any carbon atom included within the bicyclic aryl. Representative examples of the aryl groups include, but are not limited to dihydroindenyl, indenyl, naphthyl, dihydronaphthalenyl, and 5,6,7,8-tetrahydronaphthalenyl.

The term "arylalkyl" as used herein, means -alkylene-aryl where alkylene and aryl are defined herein. Such exemplified arylalkyl groups include, but are not limited to, phenylmethyl, 2,4-dimethoxyphenylmethyl, and the like.

The term "cycloalkyl" or "cycloalkane" as used herein, means a monocyclic hydrocarbon ring having three to eight carbon atoms, zero heteroatom and zero double bond and is optionally substituted. The cycloalkyl can be attached to the parent molecular moiety through any substitutable atom included within the ring. Examples of cycloalkyls include, but are not limited to, cyclopropyl, cyclobutyl, cyclopentyl, cyclohexyl, cycloheptyl, and cyclooctyl.

The term "cycloalkenyl" or "cycloalkene" as used herein, means a monocyclic hydrocarbon ring system. The monocyclic cycloalkenyl has four-, five-, six-, seven- or eight carbon atoms and zero heteroatom. The four-membered ring systems have one double bond, the five- or six-membered ring systems have one or two double bonds, and the seven- or eight-membered ring systems have one, two or three double bonds. The cycloalkenyl can be attached to the parent molecular moiety through any substitutable atom included within the ring and is optionally substituted. Representative examples of cycloalkenyl groups include, but not limited to, cyclobutenyl, cyclopentenyl, cyclohexenyl, cycloheptenyl and cyclooctenyl.

The term "halo" or "halogen" as used herein, means —Cl, —Br, —I or —F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, trifluoromethyl, pentafluoroethyl, and 2-chloro-3-fluoropentyl.

The term "heteroaryl" as used herein, means a monocyclic heteroaryl, or a bicyclic heteroaryl. The monocyclic heteroaryl is a five- or six-membered ring. The five-membered ring consists of two double bonds, and one, two, three or four nitrogen atoms and optionally one oxygen or sulfur atom. The six-membered ring consists of three double bonds and one, two, three or four nitrogen atoms. The monocyclic heteroaryl is connected to the parent molecular moiety through any substitutable atom included within the monocyclic heteroaryl. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. The bicyclic heteroaryl is connected to the parent molecular moiety through any carbon atom or any nitrogen atom included within the bicyclic heteroaryl. Representative examples of bicyclic heteroaryl groups include, but not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl quinazolinyl, quinoxalinyl and quinolinyl. The monocyclic, and bicyclic heteroaryl groups of the present invention can be substituted or unsubstituted.

The term "heteroarylalkyl" as used herein, means -alkylene-heteroaryl where alkylene and heteroaryl are defined herein. Such heteroarylalkyl groups are exemplified by pyridinylmethyl, pyridinylethyl, and the like.

The term "heterocycle" or "heterocyclic" as used herein means a monocyclic, three-, four-, five-, six- or seven-membered ring including at least one heteroatom independently selected from the group consisting of O, N, and S and the remaining are carbon atoms. The three- or four-membered ring includes zero or one double bond, and one heteroatom selected from the group consisting of O, N and S. The five-membered ring includes zero or one double bond and one, two or three heteroatoms selected from the group consisting of O, N and S. The six-membered ring includes zero, one or two double bonds and one, two or three heteroatoms selected from O, N, and S. The seven-membered ring includes zero, one, two, or three double bonds and one, two or three heteroatoms selected from O, N and S. The monocyclic heterocycle is connected to the parent molecular moiety through any carbon atom or any nitrogen atom included within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The term "heteroatom" as used herein means, but is not limited to, nitrogen, oxygen or sulfur atom.

The term "hydroxyl" or "hydroxy" as used herein means —OH.

The term "hydroxyalkyl" as used herein means, but is not limited to, an alkyl group, as defined herein, in which one, two, three, hydrogen atoms are replaced by hydroxyl groups, preferably by one hydroxyl group. Representative examples include, but are not limited to, hydroxymethyl and the like.

Particular values of variable groups in compounds of formula (I) are as follows. Such values can be used where appropriate with any of the other values, definitions, claims, or embodiments defined hereinbefore or hereinafter.

In one embodiment of the present invention, $A_1$, $A_2$, $A_4$ and $A_5$ are $C(R^1)$, wherein $R^1$ is hydrogen, alkyl, halogen or haloalkyl, and $A_3$ is $C(-L_2-R^2)$ wherein $L_2$ and $R^2$ are as defined above. Suitable alkyls for $R^1$ are selected from $C_{1-6}$ alkyls, more particularly $C_{1-3}$ alkyl such as methyl, ethyl, isopropyl or n-propyl. More particularly, $R^1$ is hydrogen or halogen.

In another embodiment, $A_1$, $A_3$, $A_4$ and $A_5$ are $C(R^1)$ wherein $R^1$ is hydrogen, alkyl, halogen or haloalkyl, and $A_2$ is $C(-L_2-R^2)$, wherein $L_2$ and $R^2$ are as defined above. Suitable alkyls for $R^1$ are selected from $C_{1-6}$ alkyls, more particularly $C_{1-3}$ alkyl such as methyl, ethyl, isopropyl or n-propyl. More particularly, $R^1$ is hydrogen or halogen.

Suitable value for $L_2$ is O or $N(R^x)$ wherein $R^x$ is hydrogen, alkyl or haloalkyl, Particularly, $R^x$ is hydrogen and $L_2$ is O.

$R^2$ is alkyl, aryl or heteroaryl. Preferably, $R^2$ is alkyl, phenyl or monocyclic heteroaryl wherein the phenyl and the monocyclic heteroaryl are unsubstituted or substituted as described herein. In one embodiment, $R^2$ is alkyl, preferably $C_{1-6}$ alkyl. More preferably, $R^2$ is $C_{1-3}$ alkyl such as methyl, ethyl, n-propyl or isopropyl.

$L_1$ is O. Alternatively $L_1$ is $N(R^x)$ wherein $R^x$ is hydrogen, alkyl or haloalkyl, particularly, $R^x$ is hydrogen.

In one embodiment, A is phenyl that is optionally further substituted with 1 or 2 substituents selected from alkyl, halogen, haloalkyl and hydroxyalkyl, particularly, $C_{1-6}$ alkyl, halogen, $C_{1-6}$ haloalkyl and $C_{1-6}$ hydroxyalkyl. In one embodiment, A is an unsubstituted phenyl.

In yet another embodiment, A is a monocyclic heteroaryl ring that is connected to $L_1$ and X through the carbon atoms in the ring. Examples of such monocyclic heteroaryl ring include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl; each of which is independently unsubstituted or further substituted with 1 or 2 substituents selected from the group consisting of alkyl, halogen, haloalkyl and hydroxyalkyl, particularly $C_{1-6}$ alkyl, halogen, $C_{1-6}$ haloalkyl and $C_{1-6}$ hydroxyalkyl. In one embodiment, A is furanyl, imidazolyl, isoxazolyl, isothiazolyl, oxadiazolyl, oxazolyl, pyrazolyl, pyrrolyl, tetrazolyl, thiadiazolyl, thiazolyl or thienyl, each of which is independently unsubstituted or substituted with substituents as described hereinbefore. In another embodiment, A is unsubstituted thiazolyl.

X is $-C(H)=N-O-(CR^yR^z)_p-NR_dR_e$ wherein $R^y$ and $R^z$ are independently hydrogen, alkyl, haloalkyl or hydroxyalkyl, p is 2 or 3, $R_d$ is hydrogen, alkyl, haloalkyl, $-C(O)$alkyl, $-C(O)NH_2$, $-C(O)N(H)(alkyl)$ or $-C(O)N(alkyl)_2$ and $R_e$ is hydrogen, alkyl, or haloalkyl. Suitably, $R^y$ and $R^z$ are independently hydrogen or $C_{1-6}$ alkyl, particularly, hydrogen or methyl, p is 2 or 3, $R_d$ is hydrogen, $C_{1-3}$ alkyl (for example methyl, ethyl, isopropyl or n-propyl), $-C(O)(C_{1-3}$ alkyl), $-C(O)NH_2$ or $-C(O)N(H)(methyl)$ and $R_e$ is hydrogen. Examples of X include $-C(H)=N-O-C(H)_2-C(H)(CH_3)-N(H)C(O)(CH_3)$, $-C(H)=N-O-C(H)_2-C(H)(CH_3)-N(H)C(O)(CH_2CH_3)$, and $-C(H)=N-O-C(H)_2-C(H)(CH_3)-N(H)C(O)N(H)(CH_3)$.

In another embodiment, X is $-O-(CR^yR^z)_p-NR_dR_e$ wherein $R^y$ and $R^z$ are independently hydrogen, alkyl, haloalkyl or hydroxyalkyl, p is 2 or 3, $R_d$ is hydrogen, alkyl, haloalkyl, $-C(O)$alkyl, $-C(O)NH_2$, $-C(O)N(H)(alkyl)$ or $-C(O)N(alkyl)_2$ and $R_e$ is hydrogen, alkyl, or haloalkyl. Suitably, $R^y$ and $R^z$ are independently hydrogen or $C_{1-6}$ alkyl, particularly, hydrogen or methyl, p is 2 or 3, $R_d$ is hydrogen, $C_{1-3}$ alkyl (for example methyl, ethyl, isopropyl or n-propyl), $-C(O)(C_{1-3}$ alkyl), $-C(O)NH_2$ or $-C(O)N(H)(methyl)$ and $R_e$ is hydrogen. Examples of X include $-O-C(H)_2-C(H)(CH_3)-N(H)C(O)(CH_3)$, $-O-C(H)_2-C(H)(CH_3)-N(H)C(O)(CH_2CH_3)$, and $-O-C(H)_2-C(H)(CH_3)-N(H)C(O)N(H)(CH_3)$.

In yet another embodiment, X is $-(CR^yR^z)_q-NR_dR_e$ wherein $R^y$ and $R^z$ are independently hydrogen, alkyl, haloalkyl or hydroxyalkyl, q is 1, 2 or 3, $R_d$ is hydrogen, alkyl, haloalkyl, $-C(O)$alkyl, $-C(O)NH_2$, $-C(O)N(H)(alkyl)$ or $-C(O)N(alkyl)_2$ and $R_e$ is hydrogen, alkyl, or haloalkyl. Suitably, $R^y$ and $R^z$ are independently hydrogen or $C_{1-6}$ alkyl, particularly, hydrogen or methyl, q is 2 or 3, $R_d$ is hydrogen, $C_{1-3}$ alkyl (for example methyl, ethyl, isopropyl or n-propyl), $-C(O)(C_{1-3}$ alkyl), $-C(O)NH_2$ or $-C(O)N(H)(methyl)$ and $R_e$ is hydrogen. Examples of X include $-CH_2CH_2-C(H)(CH_3)-N(H)C(O)(CH_3)$, $-CH_2CH_2-C(H)(CH_3)-N(H)C(O)(CH_2CH_3)$, and $-CH_2CH_2-C(H)(CH_3)-N(H)C(O)N(H)(CH_3)$.

In a further embodiment, X is $-C(H)=C(H)-(CR^yR^z)_q-NR_dR_e$ wherein $R^y$ and $R^z$ are independently hydrogen, alkyl, haloalkyl or hydroxyalkyl, q is 1, 2 or 3, $R_d$ is hydrogen, alkyl, haloalkyl, $-C(O)$alkyl, $-C(O)NH_2$, $-C(O)N(H)(alkyl)$ or $-C(O)N(alkyl)_2$ and $R_e$ is hydrogen, alkyl, or haloalkyl. Suitably, $R^y$ and $R^z$ are independently hydrogen or $C_{1-6}$ alkyl, particularly, hydrogen or methyl, q is 1, 2, or 3, particularly, q is 1; $R_d$ is hydrogen, $C_{1-3}$ alkyl (for example methyl, ethyl, isopropyl or n-propyl), $-C(O)(C_{1-3}$ alkyl), $-C(O)NH_2$ or $-C(O)N(H)(methyl)$ and $R_e$ is hydrogen. Examples of X include $-C(H)=C(H)-C(H)(CH_3)-N(H)C(O)(CH_3)$, $-C(H)=C(H)-C(H)(CH_3)-N(H)C(O)(CH_2CH_3)$, and $-C(H)=C(H)-C(H)(CH_3)-N(H)C(O)N(H)(CH_3)$.

It is appreciated that the present invention contemplates compounds of formula (I) with combinations of the above embodiments, including particular and more particular embodiments.

Accordingly, one aspect of the invention is related to compounds of formula (I), or a pharmaceutically acceptable salt, prodrug, salt of a prodrug, or a combination thereof, wherein A is phenyl that is optionally further substituted with 1 or 2 substituents selected from the group consisting of alkyl, halogen, haloalkyl and hydroxyalkyl, and $L_1$ is O. Examples of this group of compounds include those wherein A is optionally further substituted with 1 or 2 substituents selected from the group consisting of $C_{1-6}$ alkyl, halogen and $C_{1-6}$ haloalkyl, particularly methyl, ethyl, n-propyl, isopropyl, bromine, chlorine, iodine, fluorine and trifluoromethyl.

Another aspect of the invention related to compounds of formula (I), or a pharmaceutically acceptable salt, prodrug, salt of a prodrug, or a combination thereof; wherein A is phenyl, optionally further substituted with 1 or 2 substituents selected from the group consisting of methyl, ethyl, n-propyl, isopropyl, bromine, chlorine, iodine, fluorine and trifluoromethyl, $L_1$ is O, $A_1$, $A_2$, $A_4$ and $A_5$ are $C(R^1)$ wherein $R^1$ is hydrogen, alkyl, halogen or haloalkyl, $A_3$ is $C(-L_2-R^2)$, wherein $L_2$ is O or $N(H)$, particularly, $L_2$ is O; and $R^2$ is a aryl or heteroaryl; wherein the aryl or heteroaryl is independently unsubstituted or substituted as described in the summary section. Particularly, $R^1$ is hydrogen, $C_{1-6}$ alkyl or halogen, more particularly $R^1$ is hydrogen, $C_{1-3}$ alkyl such as methyl, ethyl, isopropyl or n-propyl, or halogen, more particularly, $R^1$ is hydrogen or halogen. Suitably, $R^2$ is alkyl, phenyl or monocyclic heteroaryl wherein the phenyl and the monocyclic heteroaryl are independently unsubstituted or substituted as described in the summary section. In one embodiment, $R^2$ is alkyl, suitably $C_{1-6}$ alkyl. Particularly, $R^2$ is $C_{1-3}$ alkyl (for example methyl, ethyl, n-propyl or isopropyl).

Yet another aspect of the invention is related to a group of compounds of formula (I), or a pharmaceutically acceptable salt, prodrug, salt of a prodrug, or a combination thereof, wherein A is phenyl that is optionally further substituted with 1 or 2 substituents selected from the group consisting of methyl, ethyl, n-propyl, isopropyl, bromine, chlorine, iodine, fluorine and trifluoromethyl; $L_1$ is O, $A_1$, $A_2$, $A_4$ and $A_5$ are $C(R^1)$ wherein $R^1$ is hydrogen or halogen, $A_3$ is $C(-L_2-R^2)$, wherein $L_2$ is O; $R^2$ is $C_{1-3}$ alkyl (for example methyl, ethyl, n-propyl or isopropyl); and X is $-C(H)=N-O-(CR^yR^z)_p-NR_dR_e$ wherein $R^y$ and $R^z$ are independently hydrogen, alkyl, haloalkyl or hydroxyalkyl, p is 2 or 3, $R_d$ is hydrogen, alkyl, haloalkyl, $-C(O)$alkyl, $-C(O)NH_2$, $-C(O)N(H)(alkyl)$ or $-C(O)N(alkyl)_2$ and $R_e$ is hydrogen, alkyl, or haloalkyl. Suitably, $R^y$ and $R^z$ are independently hydrogen or $C_{1-6}$ alkyl, particularly, hydrogen or methyl, p is 2 or 3, $R_d$ is hydrogen, $C_{1-3}$ alkyl (for example methyl, ethyl, isopropyl or n-propyl), —C(O)($C_{1-3}$ alkyl), —C(O)NH$_2$ or —C(O)N(H)(methyl) and $R_e$ is hydrogen. Examples of X include —C(H)=N—O—C(H)$_2$—C(H)(CH$_3$)—N(H)C(O)(CH$_3$), —C(H)=N—O—C(H)$_2$—C(H)(CH$_3$)—N(H)C(O)(CH$_2$CH$_3$), and —C(H)=N—O—C(H)$_2$—C(H)(CH$_3$)—N(H)C(O)N(H)(CH$_3$).

Yet another aspect of the invention is related to a group of compounds of formula (I), or a pharmaceutically acceptable salt, prodrug, salt of a prodrug, or a combination thereof, wherein A is phenyl, optionally further substituted with 1 or 2 substituents selected from the group consisting of methyl, ethyl, n-propyl, isopropyl, bromine, chlorine, iodine, fluorine and trifluoromethyl, $L_1$ is O, $A_1$, $A_2$, $A_4$ and $A_5$ are C($R^1$) wherein $R^1$ is hydrogen or halogen, $A_3$ is C(-$L_2$-$R^2$), wherein $L_2$ is O, $R^2$ is $C_{1-3}$ alkyl (for example methyl, ethyl, n-propyl or isopropyl); and X is —O—(C$R^yR^z$)$_p$—N$R_dR_e$ wherein $R^y$ and $R^z$ are independently hydrogen, alkyl, haloalkyl or hydroxyalkyl, p is 2 or 3, $R_d$ is hydrogen, alkyl, haloalkyl, —C(O)alkyl, —C(O)NH$_2$, —C(O)N(H)(alkyl) or —C(O)N(alkyl)$_2$ and $R_e$ is hydrogen, alkyl, or haloalkyl. Suitably, $R^y$ and $R^z$ are independently hydrogen or $C_{1-6}$ alkyl, particularly, hydrogen or methyl, p is 2 or 3, $R_d$ is hydrogen, $C_{1-3}$ alkyl (for example methyl, ethyl, isopropyl or n-propyl), —C(O)($C_{1-3}$ alkyl), —C(O)NH$_2$ or —C(O)N(H)(methyl) and $R_e$ is hydrogen. Examples of X include —O—C(H)$_2$—C(H)(CH$_3$)—N(H)C(O)(CH$_3$), —O—C(H)$_2$—C(H)(CH$_3$)—N(H)C(O)(CH$_2$CH$_3$), and —O—C(H)$_2$—C(H)(CH$_3$)—N(H)C(O)N(H)(CH$_3$).

Yet another aspect of the invention is related to a group of compounds of formula (I), or a pharmaceutically acceptable salt, prodrug, salt of a prodrug, or a combination thereof, wherein A is phenyl that is optionally further substituted with 1 or 2 substituents selected from the group consisting of methyl, ethyl, n-propyl, isopropyl, bromine, chlorine, iodine, fluorine and trifluoromethyl, $L_1$ is O, $A_1$, $A_2$, $A_4$ and $A_5$ are C($R^1$) wherein $R^1$ is hydrogen or halogen, $A_3$ is C(-$L_2$-$R^2$), wherein $L_2$ is O, $R^2$ is $C_{1-3}$ alkyl (for example methyl, ethyl, n-propyl or isopropyl); and X is —O—(C$R^yR^z$)$_q$—N$R_dR_e$ wherein $R^y$ and $R^z$ are independently hydrogen, alkyl, haloalkyl or hydroxyalkyl, q is 1, 2 or 3, $R_d$ is hydrogen, alkyl, haloalkyl, —C(O)alkyl, —C(O)NH$_2$, —C(O)N(H)(alkyl) or —C(O)N(alkyl)$_2$ and $R_e$ is hydrogen, alkyl, or haloalkyl. Suitably, $R^y$ and $R^z$ are independently hydrogen or $C_{1-6}$ alkyl, particularly, hydrogen or methyl, q is 2 or 3, $R_d$ is hydrogen, $C_{1-3}$ alkyl (for example methyl, ethyl, isopropyl or n-propyl), —C(O)($C_{1-3}$ alkyl), —C(O)NH$_2$ or —C(O)N(H)(methyl) and $R_e$ is hydrogen. Examples of X include —CH$_2$CH$_2$—C(H)(CH$_3$)—N(H)C(O)(CH$_3$), —CH$_2$CH$_2$—C(H)(CH$_3$)—N(H)C(O)(CH$_2$CH$_3$), and —CH$_2$CH$_2$—C(H)(CH$_3$)—N(H)C(O)N(H)(CH$_3$).

Yet another aspect of the invention is related to a group of compounds of formula (I), or a pharmaceutically acceptable salt, prodrug, salt of a prodrug, or a combination thereof, wherein A is phenyl that is optionally further substituted with 1 or 2 substituents selected from the group consisting of methyl, ethyl, n-propyl, isopropyl, bromine, chlorine, iodine, fluorine and trifluoromethyl, $L_1$ is O, $A_1$, $A_2$, $A_4$ and $A_5$ are C($R^1$) wherein $R^1$ is hydrogen or halogen, $A_3$ is C(-$L_2$-$R^2$), wherein $L_2$ is O, $R^2$ is $C_{1-3}$ alkyl (for example methyl, ethyl, n-propyl or isopropyl); and X is —C(H)=C(H)—(C$R^yR^z$)$_q$—N$R_dR_e$ wherein $R^y$ and $R^z$ are independently hydrogen, alkyl, haloalkyl or hydroxyalkyl, q is 1, 2 or 3, $R_d$ is hydrogen, alkyl, haloalkyl, —C(O)alkyl, —C(O)NH$_2$, —C(O)N(H)(alkyl) or —C(O)N(alkyl)$_2$ and $R_e$ is hydrogen, alkyl, or haloalkyl. Suitably, $R^y$ and $R^z$ are independently hydrogen or $C_{1-6}$ alkyl, particularly, hydrogen or methyl, q is 1, $R_d$ is hydrogen, $C_{1-3}$ alkyl (for example methyl, ethyl, isopropyl or n-propyl), —C(O)($C_{1-3}$ alkyl), —C(O)NH$_2$ or —C(O)N(H)(methyl) and $R_e$ is hydrogen. Examples of X include —C(H)=C(H)—C(H)(CH$_3$)—N(H)C(O)(CH$_3$), —C(H)=C(H)—C(H)(CH$_3$)—N(H)C(O)(CH$_2$CH$_3$), and —C(H)=C(H)—C(H)(CH$_3$)—N(H)C(O)N(H)(CH$_3$).

Yet another aspect of the invention is related to compounds of formula (I), or a pharmaceutically acceptable salt, prodrug, salt of a prodrug, or a combination thereof; wherein A is a monocyclic heteroaryl, connected to $L_1$ and X through the carbon atoms in the ring and optionally further substituted with 1 or 2 substituents selected from the group consisting of alkyl, halogen, haloalkyl and hydroxyalkyl, and $L_1$ is O. One embodiment of this group of compounds is where A is optionally further substituted with 1 or 2 substituents selected from the group consisting of $C_{1-6}$ alkyl, halogen and $C_{1-6}$ haloalkyl, particularly methyl, ethyl, n-propyl, isopropyl, bromine, chlorine, iodine, fluorine and trifluoromethyl. Suitable examples of the monocyclic heteroaryl for A are furanyl, imidazolyl, isoxazolyl, isothiazolyl, oxadiazolyl, oxazolyl, pyrazolyl, pyrrolyl, tetrazolyl, thiadiazolyl, thiazolyl and thienyl, particularly, thiazolyl.

Another aspect of the invention related to compounds of formula (I), or a pharmaceutically acceptable salt, prodrug, salt of a prodrug, or a combination thereof; wherein A is furanyl, imidazolyl, isoxazolyl, isothiazolyl, oxadiazolyl, oxazolyl, pyrazolyl, pyrrolyl, tetrazolyl, thiadiazolyl, thiazolyl or thienyl, connected to $L_1$ and X through the carbon atoms in the ring and each ring is optionally further substituted with 1 or 2 substituents selected from the group consisting of methyl, ethyl, n-propyl, isopropyl, bromine, chlorine, iodine, fluorine and trifluoromethyl, $L_1$ is O, $A_1$, $A_2$, $A_4$ and $A_5$ are C($R^1$) wherein $R^1$ is hydrogen, alkyl, halogen or haloalkyl, $A_3$ is C(-$L_2$-$R^2$), wherein $L_2$ is O or N(H), particularly, $L_2$ is O; and $R^2$ is alkyl, aryl or heteroaryl; wherein the aryl or heteroaryl is independently unsubstituted or substituted as in the summary section. Particularly, $R^1$ is hydrogen, $C_{1-6}$ alkyl or halogen, more particularly $R^1$ is hydrogen, $C_{1-3}$ alkyl such as methyl, ethyl, isopropyl or n-propyl, or halogen, more particularly, $R^1$ is hydrogen or halogen. Suitably, $R^2$ is alkyl, phenyl or monocyclic heteroaryl wherein the phenyl and the monocyclic heteroaryl are independently unsubstituted or substituted as in the summary section. In one embodiment, $R^2$ is alkyl, suitably $C_{1-6}$ alkyl, particularly $C_{1-3}$ alkyl, for example methyl ethyl, n-propyl or isopropyl.

Yet another aspect of the invention is related to a group of compounds of formula (I), or a pharmaceutically acceptable salt, prodrug, salt of a prodrug, or a combination thereof; wherein A is A is furanyl, imidazolyl, isoxazolyl, isothiazolyl, oxadiazolyl, oxazolyl, pyrazolyl, pyrrolyl, tetrazolyl, thiadiazolyl, thiazolyl or thienyl connected to $L_1$ and X through the carbon atoms in the ring and optionally further substituted with 1 or 2 substituents selected from the group consisting of methyl, ethyl, n-propyl, isopropyl, bromine, chlorine, iodine, fluorine and trifluoromethyl, $L_1$ is O, $A_1$, $A_2$, $A_4$ and $A_5$ are C($R^1$) wherein $R^1$ is hydrogen or halogen, $A_3$ is C(-$L_2$-$R^2$), wherein $L_2$ is O, $R^2$ is $C_{1-3}$ alkyl (for example methyl, ethyl, n-propyl or isopropyl); and X is —C(H)=N—O—(C$R^yR^z$)$_p$—N$R_dR_e$ wherein $R^y$ and $R^z$ are independently hydrogen, alkyl, haloalkyl or hydroxyalkyl, p is 2 or 3, $R_d$ is hydrogen, alkyl, haloalkyl, —C(O)alkyl, —C(O)NH$_2$, —C(O)N(H)(alkyl) or —C(O)N(alkyl)$_2$ and $R_e$ is hydrogen, alkyl, or haloalkyl. Suitably, $R^y$ and $R^z$ are independently hydrogen or $C_{1-6}$ alkyl, particularly, hydrogen or methyl, p is 2 or 3, $R_d$ is hydrogen, $C_{1-3}$ alkyl (for example methyl, ethyl, isopropyl or n-propyl), —C(O)(C$_{1-3}$ alkyl), —C(O)NH$_2$ or —C(O)N(H)(methyl) and R$_e$ is hydrogen. Examples of X include —C(H)=N—O—C(H)$_2$—C(H)(CH$_3$)—N(H)C(O)(CH$_3$), —C(H)=N—O—C(H)$_2$—C(H)(CH$_3$)—N(H)C(O)(CH$_2$CH$_3$), and —C(H)=N—O—C(H)$_2$—C(H)(CH$_3$)—N(H)C(O)N(H)(CH$_3$).

Yet another aspect of the invention is related to a group of compounds of formula (I), or a pharmaceutically acceptable salt, prodrug, salt of a prodrug, or a combination thereof; wherein A is A is furanyl, imidazolyl, isoxazolyl, isothiazolyl, oxadiazolyl, oxazolyl, pyrazolyl, pyrrolyl, tetrazolyl, thiadiazolyl, thiazolyl or thienyl, connected to L$_1$ and X through the carbon atoms in the ring and optionally further substituted with 1 or 2 substituents selected from the group consisting of methyl, ethyl, n-propyl, isopropyl, bromine, chlorine, iodine, fluorine and trifluoromethyl, L$_1$ is O, A$_1$, A$_2$, A$_4$ and A$_5$ are C(R$^1$) wherein R$^1$ is hydrogen or halogen, A$_3$ is C(-L$_2$-R$^2$), wherein L$_2$ is O, R$^2$ is C$_{1-3}$ alkyl (for example methyl, ethyl, n-propyl or isopropyl); and X is —O—(CR$^y$R$^z$)$_p$—NR$_d$R$_e$ wherein R$^y$ and R$^z$ are independently hydrogen, alkyl, haloalkyl or hydroxyalkyl, p is 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, p is 2 or 3, R$_d$ is hydrogen, C$_{1-3}$ alkyl (for example methyl, ethyl, isopropyl or n-propyl), —C(O)(C$_{1-3}$ alkyl), —C(O)NH$_2$ or —C(O)N(H)(methyl) and R$_e$ is hydrogen. Examples of X include —O—C(H)$_2$—C(H)(CH$_3$)—N(H)C(O)(CH$_3$), —O—C(H)$_2$—C(H)(CH$_3$)—N(H)C(O)(CH$_2$CH$_3$), and —O—C(H)$_2$—C(H)(CH$_3$)—N(H)C(O)N(H)(CH$_3$).

Yet another aspect of the invention is related to a group of compounds of formula (I), or a pharmaceutically acceptable salt, prodrug, salt of a prodrug, or a combination thereof; wherein A is furanyl, imidazolyl, isoxazolyl, isothiazolyl, oxadiazolyl, oxazolyl, pyrazolyl, pyrrolyl, tetrazolyl, thiadiazolyl, thiazolyl or thienyl, connected to L$_1$ and X through the carbon atoms in the ring and optionally further substituted with 1 or 2 substituents selected from the group consisting of methyl, ethyl, n-propyl, isopropyl, bromine, chlorine, iodine, fluorine and trifluoromethyl, L$_1$ is O, A$_1$, A$_2$, A$_4$ and A$_5$ are C(R$^1$) wherein R$^1$ is hydrogen or halogen, A$_3$ is C(-L$_2$-R$^2$), wherein L$_2$ is O, R$^2$ is C$_{1-3}$ alkyl (for example methyl, ethyl, n-propyl or isopropyl); and X is —(CR$^y$R$^z$)$_q$—NR$_d$R$_e$ wherein R$^y$ and R$^z$ are independently hydrogen, alkyl, haloalkyl or hydroxyalkyl, q is 1, 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, q is 2 or 3, R$_d$ is hydrogen, C$_{1-3}$ alkyl (for example methyl, ethyl, isopropyl or n-propyl), —C(O)(C$_{1-3}$ alkyl), —C(O)NH$_2$ or —C(O)N(H)(methyl) and R$_e$ is hydrogen. Examples of X include —CH$_2$CH$_2$—C(H)(CH$_3$)—N(H)C(O)(CH$_3$), —CH$_2$CH$_2$—C(H)(CH$_3$)—N(H)C(O)(CH$_2$CH$_3$), and —CH$_2$CH$_2$—C(H)(CH$_3$)—N(H)C(O)N(H)(CH$_3$).

Yet another aspect of the invention is related to a group of compounds of formula (I), or a pharmaceutically acceptable salt, prodrug, salt of a prodrug, or a combination thereof; wherein A is furanyl, imidazolyl, isoxazolyl, isothiazolyl, oxadiazolyl, oxazolyl, pyrazolyl, pyrrolyl, tetrazolyl, thiadiazolyl, thiazolyl or thienyl, connected to L$_1$ and X through the carbon atoms in the ring and optionally further substituted with 1 or 2 substituents selected from the group consisting of methyl, ethyl, n-propyl, isopropyl, bromine, chlorine, iodine, fluorine and trifluoromethyl, L$_1$ is O, A$_1$, A$_2$, A$_4$ and A$_5$ are C(R$^1$) wherein R$^1$ is hydrogen or halogen, A$_3$ is C(-L$_2$-R$^2$), wherein L$_2$ is O, R$^2$ is C$_{1-3}$ alkyl (for example methyl, ethyl, n-propyl or isopropyl); and X is —C(H)=C(H)—(CR$^y$R$^z$)$_q$—NR$_d$R$_e$ wherein R$^y$ and R$^z$ are independently hydrogen, alkyl, haloalkyl or hydroxyalkyl, q is 1, 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, q is 1, R$_d$ is hydrogen, C$_{1-3}$ alkyl (for example methyl, ethyl, isopropyl or n-propyl), —C(O)(C$_{1-3}$ alkyl), —C(O)NH$_2$ or —C(O)N(H)(methyl) and R$_e$ is hydrogen. Examples of X include —C(H)=C(H)—C(H)(CH$_3$)—N(H)C(O)(CH$_3$), —C(H)=C(H)—C(H)(CH$_3$)—N(H)C(O)(CH$_2$CH$_3$), and —C(H)=C(H)—C(H)(CH$_3$)—N(H)C(O)N(H)(CH$_3$).

In another aspect of the invention, there is provided a compound of formula (Ia) or a pharmaceutically acceptable salt, prodrug, salt of a prodrug or a combination thereof,

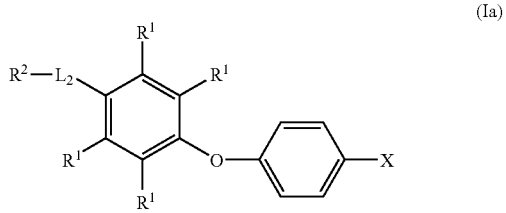

(Ia)

wherein
R$^1$ at each occurrence is independently hydrogen, alkyl, halogen or haloalkyl;
R$^2$ is alkyl, aryl or heteroaryl; wherein the aryl and heteroaryl are independently unsubstituted or substituted with 1, 2, 3, 4 or 5 substituents selected from the group consisting of —CN, —NO$_2$, alkyl, haloalkyl, —O(R$_a$), —S(R$_a$), —S(O)R$_{a'}$, —S(O)$_2$R$_{a'}$, —NR$_a$R$_b$, —OC(O)R$_{a'}$, —N(R$_b$)C(O)R$_a$, —N(R$_b$)S(O)$_2$R$_{a'}$, —N(R$_b$)C(O)OR$_a$, —N(R$_b$)C(O)NR$_a$R$_b$, —N(R$_b$)S(O)$_2$NR$_a$R$_b$, —C(O)R$_a$, —C(O)OR$_a$—C(O)NR$_a$R$_b$, —S(O)$_2$NR$_a$R$_b$, —(CR$^y$R$^z$)$_n$—CN, —(CR$^y$R$^z$)$_n$—NO$_2$, —(CR$^y$R$^z$)$_n$—O(R$_a$), —(CR$^y$R$^z$)$_n$—S(R$_a$), —(CR$^y$R$^z$)$_n$—S(O)R$_{a'}$, —(CR$^y$R$^z$)$_n$—S(O)$_2$R$_{a'}$, —(CR$^y$R$^z$)$_n$—NR$_a$R$_b$, —(CR$^y$R$^z$)$_n$—OC(O)R$_{a'}$, —(CR$^y$R$^z$)$_n$—N(R$_b$)C(O)R$_a$, —(CR$^y$R$^z$)$_n$—N(R$_b$)S(O)$_2$R$_{a'}$, —(CR$^y$R$^z$)$_n$—N(R$_b$)C(O)OR$_a$, —(CR$^y$R$^z$)$_n$—N(R$_b$)C(O)NR$_a$R$_b$, —(CR$^y$R$^z$)$_n$—N(R$_b$)S(O)$_2$NR$_a$R$_b$, —(CR$^y$R$^z$)$_n$—C(O)R$_a$, —(CR$^y$R$^z$)$_n$—C(O)OR$_a$, —(CR$^y$R$^z$)$_n$—C(O)NR$_a$R$_b$, and —(CR$^y$R$^z$)$_n$—S(O)$_2$NR$_a$R$_b$;
L$_2$ is O, N(R$^x$), S, S(O), S(O)$_2$, or C(R$^y$R$^z$)$_m$;
R$^x$ at each occurrence is independently hydrogen, alkyl or haloalkyl;
m and n at each occurrence are independently 1, 2 or 3;
R$_a$ at each occurrence is independently hydrogen, alkyl, alkenyl, haloalkyl, aryl, heteroaryl, arylalkyl or heteroarylalkyl,
R$_{a'}$ at each occurrence is independently alkyl, alkenyl, haloalkyl, aryl, heteroaryl, arylalkyl or heteroarylalkyl,
R$_b$ at each occurrence is independently hydrogen, alkyl, alkenyl or haloalkyl;
wherein the aryl, heteroaryl, aryl moiety of the arylalkyl and the heteroaryl moiety of the heteroarylalkyl as represented by R$_a$ and R$_{a'}$ are independently unsubstituted or substituted with 1, 2, 3 or 4 substituents selected from the group consisting of alkyl, haloalkyl, alkenyl, hydroxy, alkoxy, —N(H)$_2$, —N(H)(alkyl), —N(alkyl)$_2$, —C(O)H, —C(O)alkyl, —C(O)OH, —C(O)O(alkyl), —C(O)NH$_2$, —C(O)N(H)(alkyl), —C(O)N(alkyl)$_2$, —CN and —NO$_2$, X is —C(H)=N—O—(CR$^y$R$^z$)$_p$—NR$_d$R$_e$, —O—(CR$^y$R$^z$)$_p$—NR$_d$R$_e$, —(CR$^y$R$^z$)$_q$—NR$_d$R$_e$, or —C(H)=C(H)—(CR$^y$R$^z$)$_q$—NR$^d$R$_e$;

R$^y$ and R$^z$ at each occurrence are independently hydrogen, alkyl, haloalkyl or hydroxyalkyl;

p at each occurrence is independently 2 or 3;

q at each occurrence is independently 1, 2 or 3;

R$_d$ at each occurrence is independently hydrogen, alkyl, haloalkyl, —C(O)(alkyl), —C(O)N(H)$_2$, —C(O)N(H)(alkyl) or —C(O)N(alkyl)$_2$; and R$_e$ at each occurrence is independently hydrogen, alkyl or haloalkyl.

Yet another aspect of the invention is related to a group of compounds of formula (Ia) or a pharmaceutically acceptable salt, prodrug salt of a prodrug or a combination thereof wherein L$_2$ is O, R$^2$ is alkyl, phenyl or a monocyclic heteroaryl, wherein the phenyl and the monocyclic heteroaryl are independently unsubstituted or substituted as described in the summary section; and X is as defined in the summary section. Particularly, R$^2$ is alkyl; more particularly R$^2$ is C$_{1-6}$ alkyl, and even more particularly C$_{1-3}$ alkyl (for example methyl, ethyl, n-propyl or isopropyl).

Yet another aspect of the invention is related to a group of compounds of formula (Ia) or a pharmaceutically acceptable salt, prodrug, salt of a prodrug or a combination thereof wherein L$_2$ is O, R$^2$ is alkyl, and X is —C(H)=N—O—(CR$^y$R$^z$)$_p$—NR$_d$R$_e$ wherein R$^y$ and R$^z$ are independently hydrogen, alkyl, haloalkyl or hydroxyalkyl, p is 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, p is 2 or 3, R$_d$ is hydrogen, C$_{1-3}$ alkyl (for example methyl, ethyl, isopropyl or n-propyl), —C(O)(C$_{1-3}$ alkyl), —C(O)NH$_2$ or —C(O)N(H)(methyl) and R$_e$ is hydrogen. Examples of X include —C(H)=N—O—C(H)$_2$—C(H)(CH$_3$)—N(H)C(O)(CH$_3$), —C(H)=N—O—C(H)$_2$—C(H)(CH$_3$)—N(H)C(O)(CH$_2$CH$_3$), and —C(H)=N—O—C(H)$_2$—C(H)(CH$_3$)—N(H)C(O)N(H)(CH$_3$). Suitably, R$^2$ is C$_{1-6}$ alkyl, particularly C$_{1-3}$ alkyl (for example methyl, ethyl, n-propyl or isopropyl).

Yet another aspect of the invention is related to a group of compounds of formula (Ia) or a pharmaceutically acceptable salt, prodrug, salt of a prodrug or a combination thereof wherein L$_2$ is O, R$^2$ is alkyl, and X is —O—(CR$^y$R$^z$)$_p$—NR$_d$R$_e$ wherein R$^y$ and R$^z$ are independently hydrogen, alkyl, haloalkyl or hydroxyalkyl, p is 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, p is 2 or 3, R$_d$ is hydrogen, C$_{1-3}$ alkyl (for example methyl, ethyl, isopropyl or n-propyl), —C(O)(C$_{1-3}$ alkyl), —C(O)NH$_2$ or —C(O)N(H)(methyl) and R$^e$ is hydrogen. Examples of X include —O—C(H)$_2$—C(H)(CH$_3$)—N(H)C(O)(CH$_3$), —O—C(H)$_2$—C(H)(CH$_3$)—N(H)C(O)(CH$_2$CH$_3$), and —O—C(H)$_2$—C(H)(CH$_3$)—N(H)C(O)N(H)(CH$_3$). Suitably, R$^2$ is C$_{1-6}$ alkyl, particularly C$_{1-3}$ alkyl (for example methyl, ethyl, n-propyl or isopropyl).

Yet another aspect of the invention is related to a group of compounds of formula (Ia) or a pharmaceutically acceptable salt, prodrug, salt of a prodrug or a combination thereof wherein L$_2$ is O, R$^2$ is alkyl, and X is —(CR$^y$R$^z$)$_q$—NR$_d$R$_e$ wherein R$^y$ and R$^z$ are independently hydrogen, alkyl, haloalkyl or hydroxyalkyl, q is 1, 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, q is 2 or 3, R$_d$ is hydrogen. C$_{1-3}$ alkyl (for example methyl, ethyl, isopropyl or n-propyl), —C(O)(C$_{1-3}$ alkyl), —C(O)NH, or —C(O)N(H)(methyl) and R$_e$ is hydrogen. Examples of X include —CH$_2$CH$_2$—C(H)(CH$_3$)—N(H)C(O)(CH$_3$), —CH$_2$CH$_2$—C(H)(CH$_3$)—N(H)C(O)(CH$_2$CH$_3$), and —CH$_2$CH$_2$—C(H)(CH$_3$)—N(H)C(O)N(H)(CH$_3$). Suitably, R$^2$ is C$_{1-6}$ alkyl, particularly C$_{1-3}$ alkyl (for example methyl, ethyl, n-propyl or isopropyl).

Yet another aspect of the invention is related to a group of compounds of formula (Ia) or a pharmaceutically acceptable salt, prodrug, salt of a prodrug or a combination thereof wherein L$_2$ is O, R$^2$ is alkyl, and X is —C(H)=C(H)—(CR$^y$R$^z$)$_q$—NR$_d$R$_e$ wherein R$^y$ and R$^z$ are independently hydrogen, alkyl, haloalkyl or hydroxyalkyl, q is 1, 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, q is 1, R$_d$ is hydrogen, C$_{1-3}$ alkyl (for example methyl, ethyl, isopropyl or n-propyl), —C(O)(C$_{1-3}$ alkyl), —C(O)NH$_2$ or —C(O)N(H)(methyl) and R$_e$ is hydrogen. Examples of X include —C(H)=C(H)—C(H)(CH$_3$)—N(H)C(O)(CH$_3$), —C(H)=C(H)—C(H)(CH$_3$)—N(H)C(O)(CH$_2$CH$_3$), and —C(H)=C(H)—C(H)(CH$_3$)—N(H)C(O)N(H)(CH$_3$). Suitably, R$^2$ is C$_{1-6}$ alkyl, particularly C$_{1-3}$ alkyl (for example methyl, ethyl, n-propyl or isopropyl).

In another aspect of the invention, there is provided a compound of formula (Ib) or a pharmaceutically acceptable salt, prodrug, salt of a prodrug or a combination thereof,

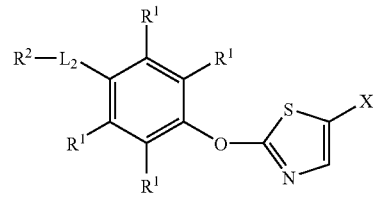

(Ib)

wherein

R$^1$ at each occurrence is independently hydrogen, alkyl, halogen or haloalkyl;

R$^2$ is alkyl, aryl or heteroaryl; wherein the aryl and the heteroaryl are independently unsubstituted or substituted with 1, 2, 3, 4 or 5 substituents selected from the group consisting of —CN, —NO, alkyl, haloalkyl, —O(R$_a$), —S(R$_a$), —S(O)R$_a$, —S(O)$_2$R$_a$, —NR$_a$R$_b$, —OC(O)R$_a$, —N(R$_b$)C(O)R$_a$, —N(R$_b$)S(O)$_2$R$_a$, —N(R$_b$)C(O)OR$_a$, —N(R$_b$)C(O)NR$_a$R$_b$, —N(R$_b$)S(O)$_2$NR$_a$R$_b$, —C(O)R$_a$, —C(O)OR$_a$, —C(O)N(R$_a$)(R$_b$), —S(O)$_2$N(R$_a$)(R$_b$), —(CR$^y$R$^z$)$_n$—CN, —(CR$^y$R$^z$)$_n$—NO$_2$, —(CR$^y$R$^z$)$_n$—O(R$_a$), —(CR$^y$R$^z$)$_n$—S(R$_a$), —(CR$^y$R$^z$)$_n$—S(O)R$_a$, —(CR$^y$R$^z$)$_n$—S(O)$_2$R$_a$, —(CR$^y$R$^z$)$_n$—NR$_a$R$_b$, —(CR$^y$R$^z$)$_n$—OC(O)R$_a$, —(CR$^y$R$^z$)$_n$—N(R$_b$)C(O)R$_a$, —(CR$^y$R$^z$)$_n$—N(R$_b$)S(O)$_2$R$_a$, —(CR$^y$R$^z$)$_n$—N(R$_b$)C(O)OR$_a$, —(CR$^y$R$^z$)$_n$—N(R$_b$)C(O)NR$_a$R$_b$, —(CR$^y$R$^z$)$_n$—N(R$_b$)S(O)$_2$NR$_a$R$_b$, —(CR$^y$R$^z$)$_n$—C(O)R$_a$, —(CR$^y$R$^z$)$_n$—C(O)OR$_a$, —(CR$^y$R$^z$)$_n$—C(O)N(R$_a$)(R$_b$), and —(CR$^y$R$^z$)$_n$—S(O)$_2$N(R$_a$)(R$_b$);

L$_2$ is O, N(R$^x$), S, S(O), S(O)$_2$, or C(R$^y$R$^z$)$_m$;

R$^x$ at each occurrence is independently hydrogen, alkyl or haloalkyl;

m and n at each occurrence are independently 1, 2 or 3;

R$_a$ at each occurrence is independently hydrogen, alkyl, alkenyl, haloalkyl, aryl, heteroaryl, arylalkyl or heteroarylalkyl, R$_{a'}$ at each occurrence is independently alkyl, alkenyl, haloalkyl, aryl, heteroaryl, arylalkyl or heteroarylalkyl, R$_b$ at each occurrence is independently hydrogen, alkyl, alkenyl or haloalkyl;

wherein the aryl, heteroaryl, aryl moiety of the arylalkyl and the heteroaryl moiety of the heteroarylalkyl as represented by R$_a$ and R$_{a'}$ are independently unsubstituted or substituted with 1, 2, 3 or 4 substituents selected from the group consisting of alkyl, haloalkyl, alkenyl, hydroxy, alkoxy, —N(H)$_2$, —N(H)(alkyl), —N(alkyl)$_2$, —C(O)H, —C(O)alkyl, —C(O)OH, —C(O)O(alkyl), —C(O)NH$_2$, —C(O)N(H)(alkyl), —C(O)N(alkyl)$_2$, —CN and —NO$_2$, X is —C(H)=N—O—(CR$^y$R$^z$)$_p$—NR$_d$R$_e$, —O—(CR$^y$R$^z$)$_p$—NR$_d$R$_e$, —(CR$^y$R$^z$)$_q$—NR$_d$R$_e$, or —C(H)=C(H)—(CR$^y$R$^z$)$_q$—NR$_d$R$_e$;

R$^y$ and R$^z$ at each occurrence are independently hydrogen, alkyl, haloalkyl or hydroxyalkyl;

p at each occurrence is independently 2 or 3;

q at each occurrence is independently 1, 2 or 3;

R$_d$ at each occurrence is independently hydrogen, alkyl, haloalkyl, —C(O)(alkyl), —C(O)N(H)$_2$, —C(O)N(H)(alkyl) or —C(O)N(alkyl)$_2$; and R$_e$ at each occurrence is independently hydrogen, alkyl or haloalkyl.

Yet another aspect of the invention is related to a group of compounds of formula (Ib) or a pharmaceutically acceptable salt, prodrug, salt of a prodrug or a combination thereof wherein L$_2$ is O, R$^2$ is alkyl, phenyl or a monocyclic heteroaryl, wherein the phenyl and the monocyclic heteroaryl are independently unsubstituted or substituted as described in the summary section, and X is as defined in the summary section. Suitably, R$^2$ is alkyl, particularly C$_{1-6}$ alkyl, and more particularly C$_{1-3}$ alkyl (for example methyl, ethyl, n-propyl or isopropyl).

Yet another aspect of the invention is related to a group of compounds of formula (Ib) or a pharmaceutically acceptable salt, prodrug, salt of a prodrug or a combination thereof wherein L$_2$ is O, R$^2$ is alkyl, and X is —C(H)=N—O—(CR$^y$R$^z$)$_p$—NR$_d$R$_e$ wherein R$^y$ and R$^z$ are independently hydrogen, alkyl, haloalkyl or hydroxyalkyl, p is 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, p is 2 or 3, R$_d$ is hydrogen, C$_{1-3}$ alkyl (for example methyl, ethyl, isopropyl or n-propyl), —C(O)(C$_{1-3}$ alkyl), —C(O)NH, or —C(O)N(H)(methyl) and R$_e$ is hydrogen. Examples of X include —C(H)=N—O—C(H)$_2$—C(H)(CH$_3$)—N(H)C(O)(CH$_3$), —C(H)=N—O—C(H)$_2$—C(H)(CH$_3$)—N(H)C(O)(CH$_2$CH$_3$), and —C(H)=N—O—C(H)$_2$—C(H)(CH$_3$)—N(H)C(O)N(H)(CH$_3$). Suitably, R$^2$ is C$_{1-6}$ alkyl, particularly C$_{1-3}$ alkyl (for example methyl, ethyl, n-propyl or isopropyl).

Yet another aspect of the invention is related to a group of compounds of formula (Ib) or a pharmaceutically acceptable salt, prodrug, salt of a prodrug or a combination thereof wherein L$_2$ is O, R$^2$ is alkyl, and X is —O—(CR$^y$R$^z$)$_p$—NR$_d$R$_e$ wherein R$^y$ and R$^z$ are independently hydrogen, alkyl, haloalkyl or hydroxyalkyl. p is 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, p is 2 or 3, R$_d$ is hydrogen, C$_{1-3}$ alkyl (for example methyl, ethyl, isopropyl or n-propyl), —C(O)(C$_{1-3}$ alkyl), —C(O)NH$_2$ or —C(O)N(H)(methyl) and R$_e$ is hydrogen. Examples of X include —O—C(H)$_2$—C(H)(CH$_3$)—N(H)C(O)(CH$_3$), —O—C(H)$_2$—C(H)(CH$_3$)—N(H)C(O)(CH$_2$CH$_3$), and —O—C(H)$_2$—C(H)(CH$_3$)—N(H)C(O)N(H)(CH$_3$). Suitably, R$^2$ is C$_{1-6}$ alkyl, particularly C$_{1-3}$ alkyl (for example methyl, ethyl, n-propyl or isopropyl).

Yet another aspect of the invention is related to a group of compounds of formula (Ib) or a pharmaceutically acceptable salt, prodrug, salt of a prodrug or a combination thereof wherein L$_2$ is O, R$^2$ is alkyl, and X is —(CR$^y$R$^z$)$_q$—NR$_d$R$_e$ wherein R$^y$ and R$^z$ are independently hydrogen, alkyl, haloalkyl or hydroxyalkyl, q is 1, 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, q is 2 or 3, R$_d$ is hydrogen, C$_{1-3}$ alkyl (for example methyl, ethyl, isopropyl or n-propyl), —C(O)(C$_{1-3}$ alkyl) —C(O)NH$_2$ or —C(O)N(H)(methyl) and R$_e$ is hydrogen. Examples of X include —CH$_2$CH$_2$—C(H)(CH$_3$)—N(H)C(O)(CH$_3$), —CH$_2$CH$_2$—C(H)(CH$_3$)—N(H)C(O)(CH$_2$CH$_3$), and —CH$_2$CH$_2$—C(H)(CH$_3$)—N(H)C(O)N(H)(CH$_3$). Suitably, R$^2$ is C$_{1-6}$ alkyl, particularly C$_{1-3}$ alkyl (for example methyl, ethyl, n-propyl or isopropyl).

Yet another aspect of the invention is related to a group of compounds of formula (Ib) or a pharmaceutically acceptable salt, prodrug, salt of a prodrug or a combination thereof wherein L$_2$ is O, R$^2$ is alkyl, and X is —C(H)=C(H)—(CR$^y$R$^z$)$_q$—NR$_d$R$_e$ wherein R$^y$ and R$^z$ are independently hydrogen, alkyl, haloalkyl or hydroxyalkyl, q is 1, 2 or 3, R$_d$ is hydrogen, alkyl, haloalkyl, —C(O)alkyl, —C(O)NH$_2$, —C(O)N(H)(alkyl) or —C(O)N(alkyl)$_2$ and R$_e$ is hydrogen, alkyl, or haloalkyl. Suitably, R$^y$ and R$^z$ are independently hydrogen or C$_{1-6}$ alkyl, particularly, hydrogen or methyl, q is 1, R$_d$ is hydrogen, C$_{1-3}$ alkyl (for example methyl, ethyl, isopropyl or n-propyl), —C(O)(C$_{1-3}$ alkyl), —C(O)NH$_2$ or —C(O)N(H)(methyl) and R$_e$ is hydrogen. Examples of X include —C(H)=C(H)—C(H)(CH$_3$)—N(H)C(O)(CH$_3$), —C(H)=C(H)—C(H)(CH$_3$)—N(H)C(O)(CH$_2$CH$_3$), and —C(H)=C(H)—C(H)(CH$_3$)—N(H)C(O)N(H)(CH$_3$). Suitably, R$^2$ is C$_{1-6}$ alkyl, particularly C$_{1-3}$ alkyl (for example methyl, ethyl, n-propyl or isopropyl).

Exemplary compounds include, but are not limited to,

N-{(2Z)-3-[4-(4-isopropoxyphenoxy)phenyl]-1-methylprop-2-enyl}acetamide;

N-{3-[4-(4-isopropoxyphenoxy)phenyl]-1-methylpropyl}acetamide;

N-{(1S)-2-[4-(4-isopropoxyphenoxy)phenoxy]-1-methylethyl}acetamide;

N-{(1S)-2-[({(1Z)-[2-(2-bromo-4-ethoxyphenoxy)-1,3-thiazol-5-yl]methylene}amino)oxy]-1-methylethyl}acetamide;

N-{(1S)-2-[({(1E)-[2-(2-bromo-4-ethoxyphenoxy)-1,3-thiazol-5-yl]methylene}amino)oxy]-1-methylethyl}propanamide;

N-{(1S)-2-[({(1E)-[2-(2-bromo-4-ethoxyphenoxy)-1,3-thiazol-5-yl]methylene}amino)oxy]-1-methylethyl}-N'-methylurea; and N-{(2E)-3-[2-(4-isopropoxyphenoxy)-1,3-thiazol-5-yl]-1-methylprop-2-enyl}acetamide; or a pharmaceutically acceptable salt, prodrug, salt of a prodrug, or a combination thereof.

Asymmetrictrically substituted carbon or sulfur atoms can exist in the compounds disclosed herein, and accordingly can exist in, and be isolated in, optically-active and racemic forms. Individual optically-active form of the compounds can be prepared for example, by synthesis from optically-active starting materials, by chiral synthesis, by enzymatic resolution, by biotransformation, or by chromatographic separation. It is to be understood that the present invention encompasses any racemic, optically-active, stereoisomeric form, or mixtures thereof, which form possesses properties useful in the inhibition of ACC activity.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration. For example, compounds of formula (I) wherein X is C(H)=C(H)—(CR$^y$R$^z$)$_q$—NR$^d$R$^e$ can exist as E isomer in which ring A and the group (CR$^y$R$^z$)$_q$—NR$^d$R$^e$ are on the opposite side of the carbon carbon carbon double bond (as depicted in formula (Ic)) or Z isomer wherein ring A and the group (CR$^y$R$^z$)$_q$—NR$^d$R$^e$ are on the same side of the carbon carbon double bond (as depicted in formula (Id)), or mixtures thereof; or in the case wherein X is —C(H)=N—O—(CR$^y$R$^z$)$_p$—NR$_d$R$_e$, compounds of formula (I) can exist as E isomer as represented by (Ie) having ring A and the O—(CR$^y$R$^z$)$_p$—NR$_d$R$_e$ group on the opposite side of the double bond, or as Z isomer as represented by (If) having ring A and the O—(CR$^y$R$^z$)$_p$—NR$_d$R$_e$ group on the same side of the double bond, or mixtures of both isomers thereof. It is to be understood that the present invention contemplates all geometric isomers, including E-isomer, Z-isomer, as well as mixtures of both isomers (equal or not equal).

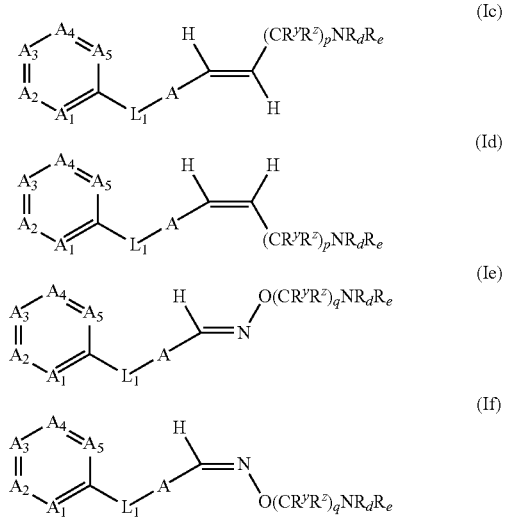

In yet another aspect of the invention, there is provided compounds of formula (Ic), (Id), (Ie) or (If), or a pharmaceutically acceptable salt, prodrug, salt of a prodrug, or a combination thereof; wherein $A_1$, $A_4$ and $A_5$ are each independently N or C(R$^1$);
one of $A_2$ and $A_3$ is C(-L$_2$-R$^2$) and the other is N or C(R$^1$); provided that no more than two of $A_1$, $A_2$, $A_3$, $A_4$ and $A_5$ are N;
R$^1$ at each occurrence is independently hydrogen, alkyl, halogen or haloalkyl;
R$^2$ is alkyl, aryl or heteroaryl; wherein the aryl and heteroaryl are independently unsubstituted or substituted with 1, 2, 3, 4 or 5 substituents selected from the group consisting of —CN, —NO$_2$, alkyl, haloalkyl, —O(R$_a$), —S(R$_a$), —S(O)R$_{a'}$, —S(O)$_2$R$_{a'}$, —NR$_a$R$_b$, —OC(O)R$_{a'}$; —N(R$_b$)C(O)R$_a$, —N(R$_b$)S(O)$_2$R$_{a'}$, —N(R$_b$)C(O)OR$_a$, —N(R$_b$)C(O)NR$_a$R$_b$, —N(R$_b$)S(O)$_2$NR$_a$R$_b$, —C(O)R$_a$, —C(O)OR$_a$—C(O)NR$_a$R$_b$, —S(O)$_2$NR$_a$R$_b$, —(CR$^y$R$^z$)$_n$—CN, —(CR$^y$R$^z$)$_n$—NO$_2$, —(CR$^y$R$^z$)$_n$—O(R$_a$), —(CR$^y$R$^z$)$_n$—S(R$_a$), —(CR$^y$R$^z$)$_n$—S(O)R$_{a'}$, —(CR$^y$R$^z$)$_n$—S(O)$_2$R$_{a'}$, —(CR$^y$R$^z$)$_n$—NR$_a$R$_b$, —(CR$^y$R$^z$)$_n$—OC(O)R$_{a'}$, —(CR$^y$R$^z$)$_n$—N(R$_b$)C(O)R$_a$, —(CR$^y$R$^z$)$_n$—N(R$_b$)S(O)$_2$R$_{a'}$, —(CR$^y$R$^z$)$_n$—N(R$_b$)C(O)OR$_a$, —(CR$^y$R$^z$)$_n$—N(R$_b$)C(O)NR$_a$R$_b$, —(CR$^y$R$^z$)$_n$—N(R$_b$)S(O)$_2$NR$_a$R$_b$, —(CR$^y$R$^z$)$_n$—C(O)R$_a$, —(CR$^y$R$^z$)$_n$—C(O)OR$_a$, —(CR$^y$R$^z$)$_n$—C(O)NR$_a$R$_b$, and —(CR$^y$R$^z$)$_n$—S(O)$_2$NR$_a$R$_b$;

$L_1$ is O, N(R$^x$), S, S(O), S(O)$_2$, or C(R$^y$R$^z$)$_m$;
$L_2$ is O, N(R$^x$), S, S(O), S(O)$_2$, or C(R$^y$R$^z$)$_m$;
R$^x$ at each occurrence is independently hydrogen, alkyl or haloalkyl;
m and n at each occurrence are independently 1, 2 or 3;
R$_a$ at each occurrence is independently hydrogen, alkyl, alkenyl, haloalkyl, aryl, heteroaryl, arylalkyl or heteroarylalkyl,
R$_{a'}$ at each occurrence is independently alkyl, alkenyl, haloalkyl, aryl, heteroaryl, arylalkyl or heteroarylalkyl,
R$_b$ at each occurrence is independently hydrogen, alkyl, alkenyl or haloalkyl;
wherein the aryl, heteroaryl, aryl moiety of the arylalkyl and the heteroaryl moiety of the heteroarylalkyl as represented by R$_a$ and R$_{a'}$, are independently unsubstituted or substituted with 1, 2, 3 or 4 substituents selected from the group consisting of alkyl, haloalkyl, alkenyl, hydroxy, alkoxy, —N(H)$_2$, —N(H)(alkyl), —N(alkyl)$_2$, —C(O)H, —C(O)alkyl, —C(O)OH, —C(O)O(alkyl), —C(O)NH$_2$, —C(O)N(H)(alkyl), —C(O)N(alkyl)$_2$, —CN and —NO$_2$,
A is phenyl or monocyclic heteroaryl, optionally further substituted with 1 or 2 substituents selected from the group consisting of alkyl, halogen, haloalkyl and hydroxyalkyl;
R$^y$ and R$^z$ at each occurrence are independently hydrogen, alkyl, haloalkyl or hydroxyalkyl;
p at each occurrence is independently 2 or 3;
q at each occurrence is independently 1, 2 or 3;
R$_d$ at each occurrence is independently hydrogen, alkyl, haloalkyl, —C(O)(alkyl), —C(O)N(H)$_2$, —C(O)N(H)(alkyl) or —C(O)N(alkyl)$_2$; and
R$_e$ at each occurrence is independently hydrogen, alkyl or haloalkyl.

It is to be understood that embodiments of the variables and combinations of embodiments, including particular and more particular embodiments, described for compounds of formula (I) are also contemplated for compounds of formula (Ic), (Id), (Ie) and (If).

Within the present invention it is to be understood that a compound of the formula (I), (Ia), (Ib), (Ic), (Id), (Ie) or (If), or a salt thereof can exhibit the phenomenon of tautomerism and that the formulae drawings within this specification can represent only one of the possible tautomeric forms. It is to be understood that the invention encompasses any tautomeric form which inhibits ACC and is not to be limited merely to any one tautomeric form utilized within the formulae drawings.

Synthetic Methods

This invention is intended to encompass compounds having formula (I), (Ia), (Ib), (Ic), (Id), (Ie) or (If) when prepared by synthetic processes or by metabolic processes. Preparation of the compounds of the invention by metabolic processes include those occurring in the human or animal body (in vivo) or processes occurring in vitro.

The synthesis of compounds of formula (I), (Ia), (Ib), (Ic), (Id), (Ie) and (If) wherein the groups $A_1$, $A_2$, $A_3$, $A_4$, $A_5$, R$^y$, $R^z$, $L_1$, A, $R_d$, $R_e$, p and q, have the meanings as set forth in the summary section unless otherwise noted, is exemplified in Schemes 1-4.

As used in the descriptions of the schemes and the examples, certain abbreviations are intended to have the following meanings: Pd (PPh$_3$)$_2$Cl$_2$ for bis(triphenylphosphine)palladium(II) dichloride, PPh$_3$ for triphenylphosphine, DMSO for dimethylsulfoxide; DBU for 1,8-diazabicyclo[5.4.0]undec-7-ene; and HPLC for high pressure liquid chromatography.

E isomer of compounds of general formula (I) wherein X is C(H)=C(H)—(CHR$^y$)NR$_d$R$_e$ can be prepared using the general procedures as outlined in Scheme 1.

monoalkylated or dialkylated with about one or two equivalents of an alkylating agents having formula R$_d$X$^a$ or R$_e$X$^a$, or sequentially with about one equivalent of R$_d$X$^a$, followed by about one equivalent of R$_e$X$^a$, wherein X$^a$ is a good leaving group such as a halogen, methanesulfonate, benzenesulfonate or p-toluenesulfonate, in the presence of a base such as a trialkylamine (e.g. triethylamine, diisopropylethylamine and the like), a tertiary cyclic amine (e.g. N-methylmorpholine. DBU and the like), or an inorganic base (e.g. carbonates of sodium or potassium, hydrogen carbonates of sodium or potassium, hydroxides of cesium, sodium or potassium, and the like). Acylation of the amines of formula (7) wherein R$_e$ is hydrogen, alkyl or haloalkyl and R$_d$ is hydrogen to provide

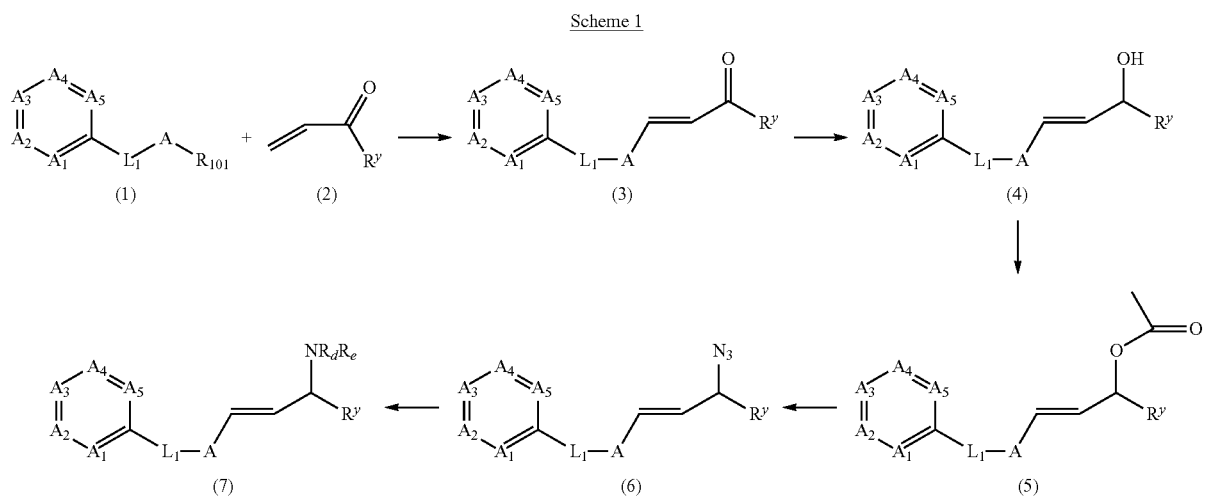

Scheme 1

Compounds of formula (1) wherein R$_{101}$ is halogen or triflate can be treated with compounds of formula (2) in the presence of triethylamine, tetrabutylammonium chloride and bis(triphenylphosphine)palladium(II) dichloride, at elevated temperature, to produce the E isomer of vinyl ketone of formula (3) after column chromatography. Reduction of compounds of formula (3) with a reducing agent such as sodium-borohydride provides the corresponding alcohols of formula (4). Acetylation of the alcohols of formula (4) with acetic anhydride in the presence of a base (for example triethylamine) and 4-(dimethylamino)pyridine, provides compounds of formula (5). Reaction of compounds of formula (5) with sodium azide in the presence of tetrakis(triphenylphosphine)palladium(0) in a solvent and elevated temperature affords compounds of formula (6). Treatment of compounds of formula (6) in a solvent such as tetrahydrofuran, with triphenylphosphine and aqueous sodium hydroxide at elevated temperature (for example, at about 50° C. to about 70° C.) afforded amines of formula (7) wherein R$_d$ and R$_e$ are hydrogen.

Compounds of formula (7) wherein R$_d$ and R$_e$ are hydrogen can be further derivatized using procedures that are known to one skilled in the art. For example, the amine can be amines of formula (7) wherein R$_e$ is hydrogen, alkyl or haloalkyl and R$_d$ is —C(O)alkyl can be accomplished by reaction with an anhydride such as acetic anhydride, or acid halides of formula (alkyl)C(O)Y wherein Y is halogen, in the presence of a base as listed in the preceding reaction. Reaction of the amines of formula (7) wherein R$_e$ is hydrogen, alkyl or haloalkyl with trichloroacetyl isocyanate in a solvent such as dichloromethane and the like, at ambient temperature, followed by refluxing in methanol in catalytic amount of sodium carbonate and water, affords ureas of formula (7) wherein R$_e$ is hydrogen, alkyl or haloalkyl and R$_d$ is —C(O)NH$_2$. Ureas of formula (7) wherein R$_e$ is hydrogen, alkyl or haloalkyl and R$_d$ is —C(O)NH(alkyl) can be prepared by treatment of (7) wherein R$_d$ is hydrogen and R$_e$ is hydrogen, alkyl or haloalkyl with isocyanates of formula (alkyl)NCO in a solvent such as dichloromethane and the like, at ambient temperature.

Compounds of formula (I) wherein X is —(CR$^y$R$^z$)$_q$NR$_d$R$_e$ or E isomer of compounds of general formula (I) wherein X is C(H)=C(H)—(CR$^y$R$^z$)$_q$NR$_d$R$_e$ can be prepared using the general procedures as outlined in Scheme 2.

Scheme 2

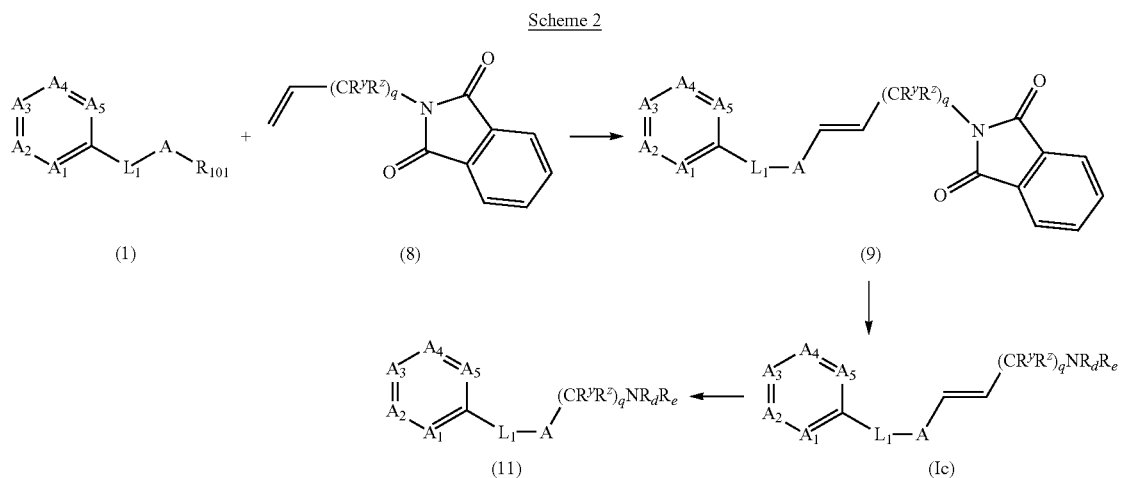

Compounds of formula (9) can be prepared from reactions of (1) and (8) using reaction conditions as outlined in Scheme I for the transformation of (1) to (3). Removal of the nitrogen protecting group can be achieved by heating compounds of formula (9) in a solvent such as ethanol and the like, with hydrazine at elevated temperature (for example, at about 40° C. to about 70° C.) to provide compounds of formula (Ic) wherein $R_d$ and $R_e$ are hydrogen. Hydrogenation of compounds of formula (Ic) wherein $R_d$ and $R_e$ are hydrogen using procedures known to one skilled in the art provide compounds of formula (11). Compounds of formulae (Ic) and (11) having at least one hydrogen atom attached to the nitrogen can be derivatized using reaction conditions outlined in Scheme 1.

Compounds of general formula (I) wherein X is —C(H)=N(O)—$(CR^yR^z)_pNR_dR_e$ can be prepared using general procedure as described in Scheme 3.

Scheme 3

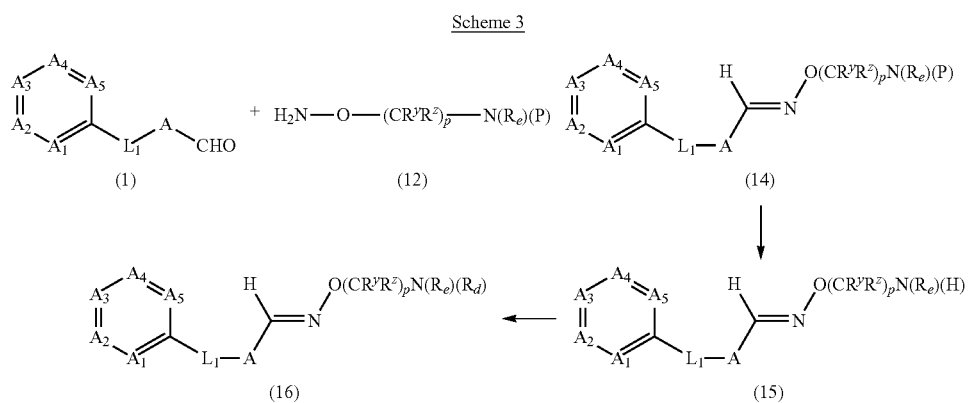

Treatment of aldehydes of formula (1) with hydroxyamines of formula (12) wherein P is a nitrogen protecting group that is compatible with the reaction conditions (e.g. tert-butoxycarbonyl) in a solvent such as tetrahydrofuran, and in the presence of an acid such as acetic acid, at elevated temperature, provides a mixture of E and Z isomers of formula (14). If desired, the isomers can be separated by techniques such as column chromatography. Deprotection of compounds of formula (14) provides compounds of formula (15). Certain deprotection techniques such as reaction with acid such as hydrogen chloride in ether can isomerizes the pure geometric isomers. Derivatization of (15) using reaction conditions as described in Scheme 1 provides compounds of formula (16). The pure geometric isomers can be isolated using column chromatography.

Starting material of formula (1) can be purchased or prepared using the general procedures as illustrated in Scheme 4.

Scheme 4

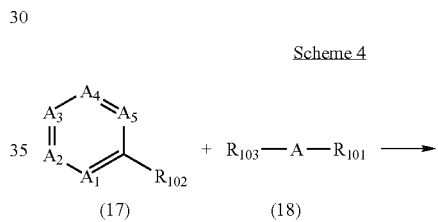

-continued

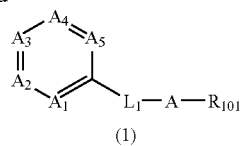

Compounds of formula (17) wherein $R_{102}$ is $L_1$-H can be reacted with compounds of formula (18) wherein $R_{103}$ is Br, Cl, or F, and $R_{101}$ is X, —CN, or halogen, in the presence of a base such as, but not limited to sodium or potassium hydride or sodium or potassium carbonate, and optionally in the presence of 18-crown-6. The reaction can generally be performed in a solvent such as, but not limited to, N,N-dimethylformamide or dimethylsulfoxide, at a temperature from about room temperature to about 180° C. The reaction can also be conducted in a microwave oven. It is appreciated compounds of formula (1) can also be obtained from the reaction of formula (17) wherein $R_{102}$ is Br, Cl, F or triflate, and compounds of formula (18) wherein $R_{103}$ is $L_1$-H.

Alternatively, the transformation can also be effected in the presence of a metal catalyst such as, but not limited to, copper metal, CuI, or palladium acetate, optionally in the presence of a ligand such as, but not limited to, 2,2'-bis(diphenylphosphino)-1,1'-binaphthyl or tri-tert-butylphosphine, and optionally in the presence of a base such as, but not limited to, pyridine, triethylamine, sodium tert-butoxide, cesium carbonate, or sodium hydride. The reaction is generally performed at a temperature from about room temperature to about 180° C. in a solvent such as, but not limited to, toluene or N,N-dimethylformamide.

It will be appreciated that the synthetic schemes and the specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the convention manner, e.g. by eliminating the solvent from the residue and further purified according to methodologies generally known in the art such as, but are not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentation, including appropriate manipulation of the reaction conditions, reagents and sequence of the synthetic route, protection of any chemical functionality that can not be compatible with the reaction conditions, and deprotection at suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of formula (I), (Ia), (Ib), (Ic), (Id), (Ie) or (If) can be accomplished by methods analogous to those described in the following schemes and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

According to a further aspect of the invention there is provided a pharmaceutical compositions including a compound of formula (I), (Ia), (Ib), (Ic), (Id), (Ic) or (If) as defined hereinbefore or a pharmaceutically acceptable salt thereof, in combination with a pharmaceutically acceptable carrier.

The pharmaceutical compositions can be formulated for oral administration in solid or liquid form, for parenteral injection or for rectal administration.

The term "therapeutically acceptable carrier" as used herein, means a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the present compounds include formulations of the same as emulsions, microemulsions, solutions, suspensions, syrups, and elixirs. In addition to the compounds, the liquid dosage forms can include diluents and/or solubilizing or emulsifying agents. Besides inert diluents, the oral compositions can include wetting, emulsifying sweetening, flavoring, and perfuming agents.

Injectable preparations of the present compounds include sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents that dissolve or disperse in the injectable media.

Inhibition of ACC by the compounds of the present invention can be delayed by using a liquid suspension of crystalline or amorphous material with poor water solubility. The rate of absorption of the compounds depends upon their rate of dissolution, which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions that are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also include buffering agents.

Suppositories for rectal administration can be prepared by mixing the compounds with a suitable non-irritating excipient that is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally include tableting lubricants and aids. Capsules can also optionally include opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

Pharmaceutically acceptable salts are well-known in the art. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that includes the hydroxy group with acid and an alkylcarboxylic acid such as acetic acid, or with acid and an arylcarboxylic acid such as benzoic acid. In the case of compounds including carboxylic acid groups, the pharmaceutically acceptable esters are prepared from compounds including the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle including one nitrogen atom. Amides derived from ammonia $C_1$-to-$C_3$ alkyl primary amides and $C_1$-to-$C_2$ dialkyl secondary amides are preferred. Amides of the compounds of formula (I), (Ia) or (Ib) can be prepared according to conventional methods. Pharmaceutically acceptable amides can be prepared from compounds including primary or secondary amine groups by reaction of the compound that includes the amino group with an alkyl anhydride, aryl anhydride, acyl halide, or aroyl halide. In the case of compounds including carboxylic acid groups, the pharmaceutically acceptable esters are prepared from compounds including the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can include a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

Compounds of the invention and pharmaceutical compositions including the same, are useful for inhibiting the effects of ACC, and more particularly that of ACC1 and ACC2. Dysregulation of fatty acids metabolism contributes to decreased insulin sensitivity and the development of metabolic syndrome. ACC is known to modulate fatty acid synthesis and fatty acid oxidation in insulin responsive tissues such as liver, adipose and skeletal muscles. The ACC inhibitors of the present invention have the potential to decrease de novo lipid synthesis and increase fat oxidation in vivo. Therefore, these compounds are useful for treating insulin resistance/type 2 diabetes, as well as obesity, hypertension and hyperlipidemia. In particular, the compounds and pharmaceutical compositions of the invention can be used for treating and preventing disorders modulated by ACC, such as but not limited to metabolic syndrome, type II diabetes, obesity, atherosclerosis and cardiovascular disease. Typically, such disorders can be ameliorated by selectively inhibiting the ACC in a mammal, preferably by administering a compound or composition of the invention, either alone or in combination with another active agent, for example, as part of a therapeutic regimen. Therefore, one embodiment of the present invention is directed to compounds of formula (I), (Ia), (Ib), (Ic), (Id), (Ie) or (If) or a pharmaceutically acceptable salt for the treatment of metabolic syndrome, type II diabetes, obesity, atherosclerosis and cardiovascular disease in a mammal.

Accordingly, a feature of the invention provides a method for inhibiting ACC (particularly ACC1, ACC2 or both) in a mammal such as human being, in need of such treatment. Such method includes administering to said mammal a compound of formula (I), (Ia), (Ib), (Ic), (Id), (Ie) or (If), or a pharmaceutically acceptable salt thereof.

Another embodiment of the present invention is directed toward a method for treating metabolic syndrome, type II diabetes, obesity, atherosclerosis or cardiovascular disease in a mammal, including administering a compound of formula (I), (Ia), (Ib), (Ic), (Id), (Ie) or (If), or a pharmaceutically acceptable salt thereof.

A further aspect of the invention is a compound of formula (I), (Ia), (Ib), (Ic), (Id), (Ie) or (If), or a pharmaceutically acceptable salt thereof, for use as a medicament for producing an inhibition of ACC (particularly ACC1 or ACC2, or both) activity in a mammal, particularly human.

Particularly, this is a compound of formula (I), (Ia), (Ib), (Ic), (Id), (Ie) or (If), or a pharmaceutically acceptable salt thereof, for use as a medicament for treating metabolic syndrome, type II diabetes, obesity, atherosclerosis or cardiovascular disease in a mammal such as human being.

Thus according to a further aspect of the invention there is provided the use of a compound of formula (I), (Ia), (Ib), (Ic), (Id), (Ie) or (If), or a pharmaceutically acceptable salt thereof, for use as a medicament for producing an inhibition of ACC (particularly ACC1 or ACC2, or both) activity in a mammal, particularly human.

Thus according to a further aspect of the invention there is provided the use of a compound of formula (I), (Ia), (Ib), (Ic), (Id), (Ie) or (If), or a pharmaceutically acceptable salt thereof, for use as a medicament for treating metabolic syndrome, type II diabetes, obesity, atherosclerosis or cardiovascular disease in a mammal such as human being.

According to a further aspect of the invention there is provided a pharmaceutical composition including a compound of formula (I), (Ia), (Ib), (Ic), (Id), (Ie) or (If), or a pharmaceutically acceptable salt thereof, in combination with a pharmaceutically acceptable carrier for use in producing an inhibition of ACC (particularly ACC1 or ACC2, or both) activity in a mammal, particularly human.

According to a further aspect of the invention there is provided a pharmaceutical composition including a compound of formula (I), (Ia), (Ib), (Ic), (Id), (Ie) or (If), or a pharmaceutically acceptable salt thereof, in combination with a pharmaceutically acceptable carrier for use in the treatment of metabolic syndrome, type II diabetes, obesity, atherosclerosis or cardiovascular disease in a mammal such as human being.

Disorders that can be treated or prevented in a patient by administering to the patient, a therapeutically effective amount of compound of the present invention in such an amount and for such time as is necessary to achieve the desired result. The term "therapeutically effective amount," refers to a sufficient amount of a compound of formula (I), (Ia), (Ib), (Ic), (Id), (Ie) or (If) to effectively ameliorate disorders by inhibiting ACC at a reasonable benefit/risk ratio applicable to any medical treatment. The specific therapeutically effective dose level for any particular patient depends upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The inhibition of ACC activity described herein can be applied as a sole therapy or in combination with one or more other substances and/or treatments for the indication being treated. Such conjoint treatment can be achieved by way of the simultaneous, sequential or separate administration of the individual components of the treatment. Simultaneous treatment can be in a single tablet or in separate tablets.

The total daily dose of the compounds of the present invention necessary to inhibit the action of ACC in single or divided doses can be in amounts, for example, from about 0.1 to 50 mg/kg body weight. In a more preferred range compounds of the present invention inhibit the action of ACC in a single or divided doses from about 1 to 25 mg/kg body weight. Single dose compositions can include such amounts or submultiple doses thereof of the compounds of the present invention to make up the daily dose. In general, treatment regimens include administration to a patient in need of such treatment from about 1 mg to about 1000 mg of the compounds per day in single or multiple doses.

Biological Data

The ACC2 enzymatic assay has been developed using either crude digitonin lysates of hACC2 overexpressing HEK 293 cells or recombinant human ACC2 expressed in baculovirus/Sf9 system. In both cases in order to increase the expression and solubility of the protein, a chimeric version of ACC2 ("mito-minus"), in which the N-terminal transmembrane domain (1-275 aa's of ACC2) was replaced with the corresponding ACC1 sequence (1-133 aa's). The enzymatic assay measures ACC mediated incorporation of [$^{14}$C] CO2 into [$^{14}$C]-Malonyl CoA. Mono-Avidin purified rat liver ACC1 was used as ACC1 enzyme source for the ACC-1 activity assay. The assay was preformed in 40 µL reaction in a 96-well plate format. The 1× assay buffer includes 50 mM Hepes/NaOH, pH 7.5, 10 mM citrate, 20 mM $MgCl_2$ and 0.075% BSA. First, 20 µL of test compounds was dissolved in 1% DMSO in 1× assay buffer was dispensed into 96-well. Then, 10 µL of enzyme in 1× assay buffer was dispensed. The reaction was initiated by adding the following substrate mixture in 1× assay buffer: 2 mM ATP, 1 mM acetyl-CoA, and 17.6 mM $NaHCO_3$ (0.12 µCi). The reaction was carried out at room temperature for 40 minutes and the reaction was terminated by adding 50 µL of 1N HCl. The plate was air-dried in a fume hood at room temperature overnight. 20 µL of distilled water was added followed by adding 150 µL of SuperMix liquid scintillation fluid (PerkinElmer). The radioactivity was determined in PerkinElmer microbeta after vigorous shaking.

The IC$_{50}$ value was calculated from 8 dose response curve of test compounds. Representative compounds of the invention inhibits ACC1 with IC$_{50}$ in the range of about 0.4 μM to > 30 μM. The compounds are also ACC2 inhibitors with IC$_{50}$ in the range of about 0.019 μM to about 15 μM.

EXAMPLES

Example 1

N-{(2Z)-3-[4-(4-isopropoxyphenoxy)phenyl]-1-methylprop-2-enyl}acetamide

Example 1A 4-isopropoxyphenol

To a mixture of hydroquinone (20.0 g, 0.182 mmol), 2-iodopropane (30.9 g, 0.182 mmol) in ethanol (25 mL) at refluxing was added KOH (88%, 12.2 mg, 0.191 mmol) in water (30 mL) over a period of 60 min. The resulting mixture was refluxed for 3 hours. The mixture was poured into 1N NaOH and extracted with ether (1×). The aqueous layer was acidified with 10% HCl to pH ~5 and extracted with ether (2×). The combined extracts were washed with brine (1×), dried over MgSO$_4$ and concentrated. The residue was purified on silica gel eluting with ethyl acetate:hexane (1:8) to give the desired product as a brownish liquid (13.01 g, 47.0%).

Example 1B 4-(4-isopropoxyphenyl)phenyl bromide

To a mixture of Example 1A (505 mg, 3.31 mmol), 1,4-dibromobenzene (2.34 g, 9.92 mmol.), K$_2$CO$_3$ (960 mg, 6.87 mmol) and pyridine (20 mL) at 80° C. was added Cu(II) oxide (650 mg, 8.17 mmol). After the addition, the mixture was refluxed vigorously for 20 h. After cooling, methylene chloride was added and the mixture was filtered through Celite. The filtrate was concentrated to dryness. The residue was dissolved in ether, which was washed with 10% HCl (2×), 1N NaOH (2×), brine (1×), dried over MgSO$_4$, and concentrated to dryness. The residue was purified on silica gel eluting with hexane and ethyl acetate gradient to give the desired product as a white solid (477 mg, 47%).

Example 1C

2-{3-[4-(4-Isopropoxy-phenoxy)-phenyl]-1-methyl-prop-2-ynyl}-isoindole-1,3-dione A mixture of Example 1B (487 mg, 1.26 mmol). 2-(1-methyl-prop-2-ynyl)-isoindole-1,3-dione (*Eur. J. Org. Chem.* 2004, 16, 3447-3458) (276 mg, 1.857 mmol), CuI (12 mg, 0.063 mmol), Pd(PPh$_3$)$_2$Cl$_2$ (45 mg, 0.064 mmol), triethylamine (1.5 mL, 10.8 mmol) in acetonitrile (6 mL) was heated under microwave at 100° C. for 30 min. The mixture was concentrated dryness by blowing nitrogen. The residue was dissolved in ethyl acetate, which was washed with water (1×), brine, dried over MgSO$_4$ and concentrated. The residue was purified on silica gel eluting with ethyl acetate and hexane gradient to give the desired product as a yellowish solid (199 mg, 37%).

Example 1D

N-{(2Z)-3-[4-(4-isopropoxyphenoxy)phenyl]-1-methylprop-2-enyl}acetamide

A mixture of Example 1C (199 mg, 0.468 mmol) and hydrazine monohydrate (140 μL, 2.39 mml) in ethanol (8 mL) was heated to reflux for 1 h. After cooling to room temperature, the reaction mixture was filtered and the filtrate concentrated. The residue was dissolved in methylene chloride and filtered again to give the desired amine as a colorless liquid (320.7 mg), which was dissolved in methylene chloride (8 mL) and cooled at 0° C. To this was added trichloroacetyl isocyanate (150 μL, 1.26 mmol) dropwise. The mixture was stirred at room temperature for 10 min. The solvent was removed under vacuum to give a yellow solid. This was dissolved in methanol (20 mL). A few mg of Na$_2$CO$_3$ and a few drops of water were added. The mixture was refluxed again for 2 h. The reaction was concentrated and the residue dissolved in ethyl acetate, which was washed with water (1×), brine (1×), dried over MgSO$_4$ and concentrated. The residue was purified on silica gel eluting with 0-5% of methanol in methylene chloride (including 10% NH$_4$OH) to give the free amine (32 mg, 23%). This compound was dissolved in tetrahydrofuran (2 mL) and triethylamine (100 μL, 0.72 mmol) was added. Acetyl chloride (10 μL, 0.141 mmol) was added dropwise at 0° C. The mixture was stirred at room temperature for 10 min. The mixture was dissolved in ether, washed with water (1×), saturated NaHCO$_3$ (1×), 10% citric acid (1×), brine (1×), dried over MgSO$_4$ and concentrated. The residue was purified on a silica gel column eluting with ethyl acetate and hexane gradient to give the desired product as a white solid (20 mg, 56%). MS (DCI): m/z 340 (M+H). $^1$H NMR (300 MHz. CDCl$_3$) δ ppm 1.28 (d, J=6.25 Hz, 3H), 1.34 (d, J=5.88 Hz, 6H), 1.94 (s. 3H), 4.42-4.54 (m, 1H), 4.93-5.08 (m, 1H), 5.44 (dd, J=11.40, 9.19 Hz, 1H), 6.41 (d, J=11.40 Hz, 1H), 6.82-7.01 (m, 6H), 7.21-7.30 (m, 2H)

Example 2

N-{3-[4-(4-isopropoxyphenoxy)phenyl]-1-methylpropyl}acetamide

Example 2A

N-{3-[4-(4-Isopropoxy-phenoxy)-phenyl]-1-methyl-propyl}-acetamide

A mixture of Example 1B (129 mg, 0.421 mmol), N-(1-methyl-prop-2-ynyl)-acetamide (60 mg, 0.540 mmol), CuI (4 mg, 0.021 mmol), Pd(PPh$_3$)$_2$Cl$_2$ (15 mg. 0.0214 mmol) and triethylamine (0.45 mL, 3.22 mmol) in acetonitrile (1.5 mL) was heated to 100° C. for 20 min under microwave. The mixture was concentrated and the residue was purified on silica gel eluting with hexane and ethyl acetate gradient to give the desired product as a white solid (66 mg).

Example 2B

N-{3-[4-(4-isopropoxyphenoxy)phenyl]-1-methylpropyl}acetamide

A mixture of 2A (20 mg, 0.05385 mmol) and 10% Pd—C (20 mg) in ethanol (3 mL) was stirred vigorously under hydrogen for 1 h. The mixture was diluted with dichloromethane, filtered through Celite and concentrated to give the desired product as a white solid (20 mg, 97%). MS (DCI):

m/z 342 (M+H), 359 (M+NH$_4$). $^1$H NMR (300 MHz, CDCl$_3$) δ ppm 1.18 (d, J=6.07 Hz, 3H), 1.33 (d, J=5.88 Hz, 6H), 1.65-1.81 (m, 2H), 1.89-1.99 (S, 3H), 2.54-2.69 (m, 2H), 3.96-4.15 (m, 1H), 4.40-4.56 (m, 1H), 5.11-5.25 (m, 1H), 6.81-6.96 (m, 6H), 7.06-7.13 (m, 2H).

Example 3

N-{(1S)-2-[4-(4-isopropoxyphenoxy)phenoxy]-1-methylethyl}acetamide

Example 3A 4-(4-Isopropoxy-phenoxy)-phenol

To a mixture of 4,4'-oxydiphenol (3.680 g, 1.82 mmol) and 2-iodopropane (1.82 mL, 1.82 mmol) in ethanol (8.0 mL) at refluxing was added KOH (88%, 1.22 g, 1.91 mmol, 1.05 equivalents) in water (4.0 mL) over a period of 10 min. The resulting mixture was refluxed for 1 hour. Ethanol was removed. The residue was dissolved in ether, which was washed with brine (1×), dried over MgSO$_4$ and concentrated. The residue was purified on a silica gel column eluting with ethyl acetate and hexane gradient to give the title product as a white solid (1.970 g, 44%)

Example 3B

{2-[4-(4-Isopropoxy-phenoxy)-phenoxy]-1-methylethyl}-carbamic acid tert-butyl ester To a solution of Example 3A (200 mg, 0.819 mmol), L-Boc-alaninal (175 mg, 0.999 mmol) and PPh$_3$ (270 mg, 1.029 mmol) in tetrahydrofuran (4 mL) was added di-ethyl azodicarboxylate (160 μL, 1.016 mmol) at room temperature. The mixture was stirred for an additional 1 h at room temperature. The mixture was concentrated and the residue was purified on a silica gel column eluting with ethyl acetate and hexane gradient to give the desired product as a liquid (224 mg, 68%).

Example 3C

N-{(1S-2-[4-(4-isopropoxyphenoxy)phenoxy]-1-methylethyl}acetamide

To a solution of Example 3B (220 mg, 0.548 mmol) in methylene chloride (3 mL) was added trifluoroacetic acid (1.0 mL) at room temperature. The mixture was stirred at room temperature for 1 h. The mixture was concentrated to dryness and co-evaporated with methanol (2×), toluene (2×) and dried under vacuum to give a viscous oil, which was dissolved in methylene chloride (4 mL), to which was added triethylamine (1.0 mL, 7.18 mmol) and acetic anhydride (200 μL, 2.11 mmol) at room temperature. The mixture was stirred overnight. The mixture was diluted with ether, which was washed with saturated NaHCO$_3$ (1×), 10% citric acid (2×), brine (1×), dried over MgSO$_4$ and concentrated. The residue was purified on a silica gel column eluting with ethyl acetate and hexane gradient to give the desired product as a white solid (148 mg, 79%). MS (DCI): m/z 344 (M+H), 361 (M+NH$_4$), $^1$H NMR (300 MHz, CDCl$_3$) δ ppm 1.31 (d, J=6.62 Hz, 3H), 1.32 (d, J=5.89 Hz, 6H), 2.00 (s, 3H), 3.81-4.02 (m, 2H), 4.41-4.52 (m, 1H), 6.80-6.97 (m, 8H).

Example 4

N-{(1S)-2-[({(1E)-[2-(2-bromo-4-ethoxyphenoxy)-1,3-thiazol-5-yl]methylene}amino)oxy]-1-methylethyl}acetamide and N-{(1S)-2-[({(1Z)-[2-(2-bromo-4-ethoxyphenoxy)-1,3-thiazol-5-yl]methylene}amino)oxy]-1-methylethyl}acetamide Example 4A 2-Bromo-4-ethoxy-phenol A solution of 2-bromo-4-ethoxyphenol (25 g, 0.181 mol) in chloroform (115 mL), cooled to 0° C. in an ice bath, was treated with bromine (10.3 mL, 0.2 mol) dropwise over 20 minutes. The resulting reaction solution was stirred at 25° C. for 2 h, charged to a separatory funnel, and washed sequentially with saturated aqueous sodium bicarbonate (2×60 mL) and brine (60 mL). The organic layer was dried (Na$_2$SO$_4$), filtered, and evaporated to provide 40 g of a pink oil. The crude product was purified by vacuum distillation (150° C., 7 mm Hg) to provide 30 g (82%) of Example 4A as a colorless oil. $^1$H NMR (300 MHz, DMSO-d$_6$) δ ppm 9.63 (s, 1H) 7.03 (d, J=2.94 Hz, 1H) 6.86 (d, J=9.0 Hz 1H) 6.77 (dd, J=9.0, 2.94 Hz, 1H) 3.92 (q, J=6.99 Hz, 2H) 1.27 (t, J=6.99 Hz, 3H).

Example 4B 2-(2-Bromo-4-ethoxy-phenoxy)-thiazole-5-carbonitrile

A solution of Example 4A (3.94 g, 0.018 mol) in N,N-dimethylformamide (20 mL) was treated with K$_2$CO$_3$ (2.86 g, 0.02 mol) followed by 2-chloro-5-cyanothiazole (2.5 g, 0.017 mol) (Adams, A. et al. J. Chem. Soc., 1956, 1870-7.) and the resulting mixture was stirred at 25° C. for 5 h. The reaction was poured into water (250 mL) and the resulting mixture stirred at 25° C. for 1 h. The mixture was filtered and the solids collected were washed with water and dried in a vacuum oven at 60° C. to provide 5.4 g (97%) of Example 4B as a tan solid. $^1$H NMR (300 MHz, DMSO-d$_6$) δ ppm 8.24 (s, 1H) 7.56 (d, J=8.82 Hz, 1H) 7.37 (d, J=2.94 Hz, 1H) 7.08 (dd, J=8.82, 2.94 Hz, 1H) 4.09 (q, J=6.99 Hz, 2 H) 1.33 (t, J=6.80 Hz, 3H); MS (DCI/NH$_3$) m/z 327 (M+H)$^+$.

Example 4C 2-(2-Bromo-4-ethoxy-phenoxy)-thiazole-5-carbaldehyde

A solution of Example 4B (700 mg, 2.15 mmol) in dichloromethane (8 mL) cooled to −78° C. was treated with diisobutylaluminum hydride (1 M in dichloromethane, 3.76 mL, 3.76 mmol) dropwise over 15 minutes and the reaction stirred at −78° C. for 45 minutes. The reaction mixture was poured into 1N HCl (50 mL) and the resulting mixture was stirred at 25° C. for 1 h. The bilayer was treated with dichloromethane (75 mL) and charged to a separatory funnel where the layers were allowed to separate. The organic layer was washed with 7% aqueous CF$_3$COOH (1×50 mL) and brine (1×50 mL) dried (Na$_2$SO$_4$), filtered and evaporated to provide 660 mg of dark yellow solids. The residue was purified by flash chromatography on silica gel eluting with a solvent gradient from 3% to 20% ethyl acetate in hexanes to provide 525 mg (75%) of Example 4C as a pale yellow solid. $^1$H NMR (300 MHz, DMSO-d$_6$) δ ppm 9.88 (s, 1H) 8.28 (s, 1H) 7.54 (d, J=8.82 Hz, 1H) 7.37 (d, J=2.94 Hz, 1H) 7.08 (dd, J=8.82, 2.94 Hz, 1H) 4.09 (q, J=6.99 Hz, 2H) 1.34 (t, J=6.99 Hz, 3H); MS (DCI/NH$_3$) m/z 329.8 (M+H)$^+$.

Example 4D tert-butyl(1S)-2-[(1,3-dioxo-1,3-dihydro-2H-isoindol-2-yl)oxy]-1-methylethylcarbamate A mixture of N-hydroxyphthalimide (2 g, 12.27 mmol), (S)-(−)-2-(tert-Butoxycarbonylamino)-1-propanol (2.25 g, 12.9 mmol), and PS-triphenylphosphine (3 mmol/g, 6.97 g, 20.9 mmol) in tetrahydrofuran (80 mL) was treated with a solution of diisopropyl azodicarboxylate (3.36 mL, 17.2 mmol) in tetrahydrofuran (30 mL) dropwise over 20 minutes. The resulting mixture was stirred at 25° C. for 18 h and concentrated under reduced pressure on a rotary evaporator to provide ~8 g of a brown oil. The residue was purified by flash chromatography on silica gel eluting with a solvent gradient from 3% to 35% ethyl acetate in hexanes to provide 2.9 g (74%) of Example 4D as a white solid. $^1$H NMR (300 MHz, CDCl$_3$) δ ppm 7.82-7.87 (m, 2H) 7.73-7.78 (m, 2H) 5.15 (br.s, 1 H) 4.21-4.29 (m, 1H) 4.12-4.18 (m, 1H) 3.89-4.02 (m, 1H) 1.43 (s, 9H) 1.36 (d, J=6.62 Hz, 3H); MS (DC/NH$_3$) m/z 321.1 (M+H)$^+$.

Example 4E tert-butyl(1S)-2-(aminooxy)-1-methylethylcarbamate

A solution of Example 4D (2.3 g, 7.21 mmol) in ethanol (60 mL) and dichloromethane (40 mL) was treated with hydrazine hydrate (1.0 mL, 21.6 mmol) and the reaction was heated at 50° C. for 1 h. The resulting suspension was stirred at 25° C. for 1 h and filtered. The filtrate was concentrated under reduced pressure on a rotary evaporator and the residue was treated with dichloromethane (~25 mL). The resulting suspension was filtered and the filtrate concentrated under reduced pressure on a rotary evaporator to provide 1.4 g of colorless oil. The crude product was purified by flash chromatography on silica gel eluting with 50% ethyl acetate in hexanes to provide 0.92 g (67%) of Example 1e as a white solid. $^1$H NMR (300 MHz, CDCl$_3$) δ ppm 5.57 (br.s, 2H) 4.60-4.70 (m, 1H) 3.89-4.05 (m, 1H) 3.59-3.70 (m, 1H) 3.42-3.53 (m, 1H) 1.45 (s, 9H) 1.12 (d, J=6.62 Hz, 3H); MS (DCI/NH$_3$) m/z 191.0 (M+H)$^+$.

Example 4F tert-butyl(1S)-2-[({(1E)-[2-(2-bromo-4-ethoxyphenoxy)-1,3-thiazol-5-yl]methylene}amino)oxy]-1-methylethylcarbamate and tert-butyl(1S)-2-[({(1Z)-[2-(2-bromo-4-ethoxyphenoxy)-1,3-thiazol-5-yl]methylene}amino)oxy]-1-methylethylcarbamate A solution of Example 4C (440 mg, 1.35 mmol) in tetrahydrofuran (6 mL) was treated with Example 4E (409 mg, 2.15 mmol) and acetic acid (131 µL, 2.29 mmol). The resulting mixture was heated at 50° C. for 1 h and stirred at 25° C. for 16 h. The reaction was concentrated under reduced pressure on a rotary evaporator to provide a separable 3:1 mixture of Z/E oxime isomers. The residue was purified by flash chromatography on silica gel eluting with a solvent gradient from 3% to 35% ethyl acetate in hexanes to provide 153 mg (23%) of the E-oxime and 475 mg (71%) of the Z-oxime as clear colorless oils. $^1$H NMR (300 MHz, DMSO-d$_6$) δ ppm (E-oxime):8.36 (s, 1H) 7.54 (s, 1H) 7.49 (d, J=8.82 Hz, 1H) 7.34 (d, J=2.94 Hz, 1H) 7.06 (dd, J=8.82, 2.94 Hz, 1H) 6.72 (d, J=8.46 Hz, 1H) 4.08 (q, J=6.99 Hz, 2H) 3.78-3.95 (m, 2H) 3.63-3.75 (m, 1H) 1.28-1.40 (m, 12H) 1.00 (d, J=6.62 Hz, 3H); MS (ESI) m/z 500.1 (M+H)$^+$. Z-oxime:1H NMR (300 MHz, DMSO-d$_6$) δ ppm 7.89 (s, 1H) 7.71 (s, 1H) 7.44 (d, J=8.82 Hz, 1H) 7.32 (d, J=2.94 Hz, 1 H) 7.04 (dd, J=8.82. 2.94 Hz, 1H) 6.76 (d, J=8.09 Hz, 1H) 3.91-4.16 (m, 4H) 3.67-3.87 (m, 1H) 1.28-1.39 (m, 12H) 1.01 (d, J=6.62 Hz, 3H); MS (ESI) m/z 500.1 (M+H)$^+$.

Example 4G 2-(2-bromo-4-ethoxyphenoxy)-1,3-thiazole-5-carbaldehyde O-[(2S)-2-aminopropyl]oxime A solution of the E-oxime from Example 4F (118 mg, 0.236 mmol) in 2M HCl/ether (2.4 mL) was stirred at 25° C. for 3 h. The resulting suspension was concentrated under reduced pressure on a rotary evaporator and dried to constant weight under vacuum to provide 101 mg (98%) of the hydrochloride salt of the desired product as a 3:1 mixture of Z/E oxime isomers. $^1$H NMR (300 MHz, DMSO-d$_6$) δ ppm 8.44 (s, E aldoxime H), 8.00* (s, Z aldoxime H) 7.95* (br s, 3H) 7.80, (s, thiazole H, Z-oxime) 7.63, (s, thiazole H, E-oxime) 7.44-7.55 (m, 1H) 7.35 (d, J=2.94 Hz, 1H) 7.06 (dd, J=9.19, 2.94 Hz, 1H) 4.21 (d, J=5.88 Hz, 2H) 3.96-4.16 (m, 3H) 1.34 (t, J=6.99 Hz, 3H) 1.11-1.24 (m, 3H) (*: overlapped signals); MS (ESI) m/z 401.9.

Example 4H

N-{(1S)-2-[({(1E)-[2-(2-bromo-4-ethoxyphenoxy)-1,3-thiazol-5-yl]methylene}amino)oxy]-1-methylethyl}acetamide and N-{(1S)-2-[({(1Z)-[2-(2-bromo-4-ethoxyphenoxy)-1,3-thiazol-5-yl]methylene}amino)oxy]-1-methylethyl}acetamide A solution of Example 4G (50 mg, 0.115 mmol) in dichloromethane (2 mL) was treated with triethylamine (0.080 mL, 0.575 mmol) followed by acetyl chloride (0.0181 mL, 0.253 mmol). The reaction was stirred at 25° C. for 2 h and was concentrated under reduced pressure on a rotary evaporator. The concentrate was purified by reverse-phase HPLC on a Waters Sunfire C18 column (1.9×10 cm, 5 µm particle size) using a gradient of 5% to 95% acetonitrile:0.1% aqueous trifluoroacetic acid to provide 12 mg (24%) of the E-oxime and 25 mg (49%) of the Z-oxime as white solids.
E-oxime: $^1$H NMR (300 MHz, DMSO-d$_6$) δ ppm 8.37 (s, 1H) 7.78 (d, J=7.72 Hz, 1H) 7.54 (s, 1H) 7.49 (d, J=8.82 Hz, 1H) 7.34 (d, J=2.94 Hz, 1H) 7.06 (dd, J=8.82, 2.94 Hz, 1H) 4.09 (q, J=6.86 Hz, 2H) 3.80-4.02 (m, 3H) 1.77 (s, 3H) 1.33 (t, J=6.99 Hz, 3H) 1.02 (d, J=6.62 Hz, 3H); MS (ESI) m/z 444.0 (M+H)$^+$. Z-oxime: $^1$H NMR (300 MHz, DMSO-d$_6$) δ ppm 7.89 (s, 1H) 7.72-7.78 (m, 2H) 7.48 (d, J=8.82 Hz, 1H) 7.33 (d, J=2.94 Hz, 1H) 7.05 (dd, J=8.82, 2.94 Hz, 1H) 3.98-4.14 (m, 5H) 1.72 (s, 3H) 1.34 (t, J=6.99 Hz, 3H) 1.02 (d, J=6.25 Hz, 3H); MS (ESI) m/z 444.0 (M+H)$^+$.

Example 5

N-{(1S)-2-[({(1E)-[2-(2-bromo-4-ethoxyphenoxy)-1,3-thiazol-5-yl]methylene}amino)oxy]-1-methylethyl}propanamide A solution of Example 4G (50 mg, 0.115 mmol) in dichloromethane (2 mL) was treated with triethylamine (0.080 mL, 0.575 mmol) followed by propionyl chloride (0.020 mL, 0.23 mmol). The reaction was stirred at 25° C. for 2 h and was concentrated under reduced pressure on a rotary evaporator.

The concentrate was purified by reverse-phase HPLC on a Waters Sunfire C18 column (1.9×10 cm, 5 μm particle size) using a gradient of 5% to 95% acetonitrile:0.1% aqueous trifluoroacetic acid to provide 8 mg (15%) of the E-oxime as a white solid. $^1$H NMR (300 MHz, DMSO-$d_6$) δ ppm 8.37 (s, 1H) 7.66 (d, J=7.72 Hz, 1H) 7.54 (s, 1H) 7.49 (d, J=9.19 Hz, 1H) 7.34 (d, J=2.94 Hz, 1H) 7.06 (dd, J=8.82, 2.94 Hz, 1H) 4.09 (q, J=6.99 Hz, 2H) 3.80-4.04 (m, 3H) 2.03 (q, J=7.48 Hz, 2H) 1.33 (t, J=6.99 Hz, 3H) 1.02 (d, J=6.62 Hz, 3H) 0.95 (t, J=7.54 Hz, 3H); MS (ESI) m/z 458.0 (M+H)$^+$.

Example 6

N-{(1S)-2-[({(1E)-[2-(2-bromo-4-ethoxyphenoxy)-1,3-thiazol-5-yl]methylene}amino)oxy]-1-methylethyl}-N'-methylurea A solution of Example 4G (50 mg, 0.115 mmol) in dichloromethane (2 mL) was treated with triethylamine (0.040 mL, 0.288 mmol) followed by methyl isocyanate (39 mg, 0.69 mmol). The reaction was stirred at 25° C. for 2 h and was concentrated under reduced pressure on a rotary evaporator. The concentrate was purified by reverse-phase HPLC on a Waters Sunfire C18 column (1.9×10 cm, 5 μm particle size) using a gradient of 5% to 95% acetonitrile:0.1% aqueous trifluoroacetic acid to provide 12 mg (23%) of the E-oxime as a white solid. 1H NMR (300 MHz, CD$_3$OD) δ ppm 8.21 (s, 1H) 7.37 (s, 1H) 7.33 (d, J=8.82 Hz, 1H) 7.26 (d, J=2.57 Hz, 1H) 7.01 (dd, J=8.82, 2.94 Hz, 1H) 3.90-4.17 (m, 8 H) 1.41 (t, J=6.99 Hz, 3H) 1.12 (d, J=6.62 Hz, 3H), MS (ESI) m/z 459.1 (M+H)$^+$.

Example 7

N-{(2E)-3-[2-(4-isopropoxyphenoxy)-1,3-thiazol-5-yl]-1-methylprop-2-enyl}acetamide Example 7A 2-(4-isopropoxyphenoxy)-1,3-thiazole To a solution of 4-isopropoxyphenol (CAS #7495-77-4. 3 g, 19.7 mmole), at room temperature in DMSO (30 mL) was added in turn, 2-bromothiazole (3.23 g, 19.7 mmole) and potassium carbonate (5.44 g, 39.4 mmole), heated at 160° C. for 3 hours. The reaction mixture was cooled, diluted with ethyl acetate, washed with water and brine sequentially, dried over magnesium sulfate, filtered and concentrated. The residue was purified on Silica gel column using a gradient of 5 to 25% ethyl acetate in hexane and provided 2.54 g (55%) of the title compound as yellowish oil. $^1$H NMR (300 MHz, CDCl$_3$) δ ppm 7.22 (d, J=3.68 Hz, 1H) 7.15-7.21 (m, 2H) 6.86-6.95 (m, 2H) 6.76 (d, J=4.04 Hz, 1H) 4.43-4.60 (heptet, J=6.25 Hz, 1H) 1.34 (d, J=6.25 Hz, 6H). MS (ESI) m/z 236 (M+H)$^+$.

Example 7B 5-iodo-2-(4-isopropoxyphenoxy)-1,3-thiazole

To a solution of the product from Example 7A (1.52 g, 6.5 mmole) in tetrahydrofuran (80 mL) at −78° C. was added a solution of 2.5M n-butyl lithium in hexane (2.84 mL, 7.1 mmole) and stirred for 2 hours. Solid iodine (1.80 g, 7.1 mmole) was added and the mixture was allowed to warm up to room temperature for an hour. The reaction mixture was diluted with ethyl acetate and added an aqueous solution of 10% sodium thiosulfate. The ethyl acetate layer was dried over magnesium sulfate, dried over magnesium sulfate and filtered through silica gel to remove polar impurities. The silica gel was washed with ethyl acetate until no UV active spot was apparent on TLC plate. Evaporation of the solvent yielded the title compound as light-yellow oil, 2.30 g (Quantitative). 1H NMR (300 MHz, CDCl$_3$) δ ppm 7.29 (s, 1H) 7.09-7.22 (m, 2H) 6.84-6.96 (m, 2H) 4.42-4.61 (heptet, J=5.88 Hz, 1H) 1.34 (d, J=5.88 Hz, 6H). MS (ESI) m/z 362 (M+H)$^+$.

Example 7C (3E)-4-[2-(4-isopropoxyphenoxy)-1,3-thiazol-5-yl]but-3-en-2-one

To a solution of the product from Example 7B (1.6 g, 4.43 mmole) in N,N-dimethylformamide (25 mL) was consecutively added triethylamine (8 mL), tetrabutyl ammonium chloride (1.2 g, 4.3 mmole), methylvinylketone (2 g, 28.5 mmole) and dichlorobis(triphenylphosphine)palladium(II) (155 mg, 0.22 mmole). The reaction mixture was heated at 75° C. overnight. The reaction mixture was diluted with ethyl acetate and washed with 0.5N aqueous HCl, followed by brine. The reaction mixture was dried over magnesium sulfate filtered and evaporated. The product was purified via silica column, using a gradient of 5-25% ethyl acetate in hexane, to yield 1.15 g (85%) of orange solid. $^1$H NMR (300 MHz, CDCl$_3$) δ ppm 7.50 (d, J=15.44 Hz, 1H) 7.42 (s, 1H) 7.13-7.24 (m, 2 H) 6.84-7.00 (m, 2H) 6.23 (d, J=15.81 Hz, 1H) 4.38-4.63 (m, 1H) 2.30 (s, 3H) 1.35 (t, J=5.52 Hz, 6H). Mass spectrum DCI 304 (M+H)$^+$.

Example 7D (3E)-4-[2-(4-isopropoxyphenoxy)-1,3-thiazol-5-yl]but-3-en-2-ol

To a suspension of the product from Example 7C (1.4 g 4.6 mmole) in methanol (45 mL) at 0° C. was added a methanolic solution of 0.4 M cerium(III)chloride (13.8 mL, 5.5 mmole) followed by portion-wise addition of sodium borohydride (175 mg, 4.6 mmole). The reaction mixture was allowed to warm up to room temperature, stirred at room temperature for 15 minutes and quenched with acetone for 30 minutes. The reaction mixture was diluted with ethyl acetate and washed with water (×2) and brine. The reaction mixture was dried over magnesium sulfate filtered and evaporated. The crude product (1.4 g, quantitative) was carried on to the next step without further purification. $^1$H NMR (300 MHz, CDCl$_3$) δ ppm 1.32 (d, J=6.62 Hz, 3H) 1.34 (d, J=6.25 Hz, 6H) 1.56 (d, J=4.04 Hz, 1H) 4.33-4.46 (m, 1H) 4.47-4.59 (m, 1H) 5.82 (dd, J=15.63, 6.07 Hz, 1H) 6.56 (d, J=16.18 Hz, 1H) 6.83-6.97 (m, 2H) 7.05 (s, 1H) 7.11-7.22 (m, 2H). Mass spectrum DCI 306 (M+H)$^+$.

Example 7E (2E)-3-[2-(4-isopropoxyphenoxy)-1,3-thiazol-5-yl]-1-methylprop-2-enyl acetate To a solution of the product from Example 7D (200 mg, 0.65 mmole) in dichloromethane (10 mL) at room temperature, was added triethylamine (750 μL) followed by acetic anhydride (300 μL, 3.2 mmole) and 4-(dimethylamino)pyridine (5 mg). The reaction mixture was stirred at room temperature, overnight and quenched with methanol for an hour.

The solvent was evaporated in vacuum and the product was purified via silica column, using a gradient of 5-20% ethyl acetate in hexane. Yield of the clear oil, 165 mg (72.5%). $^1$H NMR (300 MHz, CDCl$_3$) δ ppm 1.35 (d, J=6.25 Hz, 6H) 1.35 (d, J=6.62 Hz, 3H) 2.06 (s, 3H) 4.40-4.63 (m, 1H) 5.35-5.50 (m, 1H) 5.73 (dd, J=15.81, 6.62 Hz, 1H) 6.57 (d, J=15.81 Hz, 1H) 6.84-6.96 (m, 2H) 7.07 (s, 1H) 7.12-7.22 (m, 2 H). Mass spectrum DCI 348 (M+H)$^+$.

Example 7F

5-[(1E)-3-azidobut-1-enyl]-2-(4-isopropoxyphenoxy)-1,3-thiazole

To a solution of the product of Example 7E (155 mg, 0.45 mmole) in tetrahydrofuran (15 mL) was added sodium azide (32 mg, 0.5 mmole) and tetrakis(triphenylphosphine)palladium(0) (25 mg, 0.022 mmole) and heated at 50° C. After 2 hours additional sodium azide (23 mg, 0.35 mmole) was added and after 8 hours a third amount of sodium azide (40 mg, 0.61 mmole) was added and stirred at 50° C. overnight. The reaction mixture was added ether and hexane and the organic phase was washed twice with water followed by brine. The reaction mixture was dried over magnesium sulfate filtered and evaporated. The product was purified via silica column, using a gradient of 5-25% ethyl acetate in hexane and yielded 85 mg (57.6%) of clear oil. 1H NMR (300 MHz, CDCl$_3$) δ ppm 7.13-7.22 (m, 2H) 7.10 (s, 1H) 6.86-6.98 (m, 2H) 6.58 (d, J=15.44 Hz, 1H) 5.69 (dd, J=15.63, 7.17 Hz, 1H) 4.42-4.62 (m, 1H) 3.96-4.23 (m, 1H) 1.35 (d, J=5.88 Hz, 6H) 1.33 (d, J=5.88 Hz, 3H). Mass spectrum DCI 331 (M+H)$^+$.

Example 7G

N-{(2E)-3-[2-(4-isopropoxyphenoxy)-1,3-thiazol-5-yl]-1-methylprop-2-enyl}acetamide To a solution of the product of Example 7F (85 mg, 0.26 mmole) in tetrahydrofuran (3 mL)) was added triphenylphosphine (75 mg, 0.29 mmole) and stirred at 50° C. for 3.5 hours. The reaction mixture was added an aqueous solution of 2N NaOH (0.3 mL) and stirring was continued at 50° C. for additional 40 minutes. The reaction mixture was cooled down to room temperature, added acetic anhydride (200 µL, 2.1 mmole), stirred for 45 minutes, quenched with methanol and stirred at room temperature, overnight. The reaction mixture was diluted with methylene chloride and washed with water (×3) and brine. The product was purified via silica column, using a gradient of 25-100% ethyl acetate in hexane and yielded 40 mg (44.9%) of light yellow oil. $^1$H NMR (300 MHz, CDCl$_3$) δ ppm 7.11-7.22 (m, 2H) 7.04 (s, 1H) 6.85-6.95 (m, 2H) 6.48 (dd, J=15.44, 1.10 Hz, 1H) 5.72 (dd, J=15.63, 5.70 Hz, 1H) 5.37 (d, J=8.46 Hz, 1H) 4.60-4.76 (m, 1H) 4.44-4.59 (m, 1H) 2.00 (s, 3H) 1.34 (d, J=6.25 Hz, 6H) 1.28 (d, J=6.62 Hz, 3H). Mass spectrum DCI 347 (M+H)$^+$.

It is understood that the foregoing detailed description and accompanying examples are merely illustrative and are not to be taken as limitations upon the scope of the invention, which is defined solely by the appended claims and their equivalents. Various changes and modifications including, but not limited to, those relating to the chemical structures, substituents, derivatives, intermediates, syntheses, formulations and/or methods of use of the invention, can be made without departing from the spirit and scope thereof.

What we claim is:

1. A compound of formula (I), or a pharmaceutically acceptable salt, prodrug, salt of a prodrug, or a combination thereof

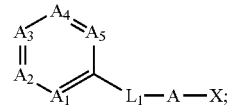

wherein $A_1$, $A_4$ and $A_5$ are each $C(R^1)$;

one of $A_2$ and $A_3$ is $C(-L_2-R^2)$ and the other is N or $C(R^1)$;

$R^1$ at each occurrence is independently hydrogen, alkyl, halogen or haloalkyl;

$R^2$ is alkyl, aryl or heteroaryl; wherein the aryl and heteroaryl are independently unsubstituted or substituted with 1, 2, 3, 4 or 5 substituents selected from the group consisting of —CN, —NO$_2$, alkyl, haloalkyl, —O(R$_a$), —S(R$_a$), —S(O)R$_{a'}$, —S(O)$_2$R$_{a'}$, —NR$_a$R$_b$, —OC(O)R$_{a'}$, —N(R$_b$)C(O)R$_a$, —N(R$_b$)S(O)$_2$R$_{a'}$, —N(R$_b$)C(O)OR$_a$, —N(R$_b$)C(O)NR$_a$R$_b$, —N(R$_b$)S(O)$_2$NR$_a$R$_b$, —C(O)R$_a$, —C(O)OR$_a$, —C(O)NR$_a$R$_b$, —S(O)$_2$NR$_a$R$_b$, —(CR$^y$R$^z$)$_n$—CN, —(CR$^y$R$^z$)$_n$—NO$_2$, —(CR$^y$R$^z$)$_n$—O(R$^a$), —(CR$^y$R$^z$)$_n$—S(R$^a$), —(CR$^y$R$^z$)$_n$—S(O)R$_{a'}$, —(CR$^y$R$^z$)$_n$—S(O)$_2$R$_{a'}$, —(CR$^y$R$^z$)$_n$—NR$_a$R$_b$, —(CR$^y$R$^z$)$_n$—OC(O)R$_{a'}$, —(CR$^y$R$^z$)$_n$—N(R$_b$)C(O)R$_a$, —(CR$^y$R$^z$)$_n$—N(R$^b$)S(O)$_2$R$_{a'}$, —(CR$^y$R$^z$)$_n$—N(R$_b$)C(O)OR$_a$, —(CR$^y$R$^z$)$_n$—N(R$_b$)C(O)NR$_a$R$_b$, —(CR$^y$R$^z$)$_n$—N(R$^b$)S(O)$_2$NR$_a$R$_b$, —(CR$^y$R$^z$)$_n$—C(O)R$_a$, —(CR$^y$R$^z$)$_n$—C(O)OR$_a$, —(CR$^y$R$^z$)$_n$—C(O)NR$_a$R$_b$, and —(CR$^y$R$^z$)$_n$—S(O)$_2$NR$_a$R$_b$;

$L_1$ is O;

$L_2$ is O or $C(R^yR^z)_m$;

$R^x$ at each occurrence is independently hydrogen, alkyl or haloalkyl;

m and n at each occurrence are independently 1, 2 or 3;

$R_a$ at each occurrence is independently hydrogen, alkyl, alkenyl, haloalkyl, aryl, heteroaryl, arylalkyl or heteroarylalkyl, $R_{a'}$ at each occurrence is independently alkyl, alkenyl, haloalkyl, aryl, heteroaryl, arylalkyl or heteroarylalkyl, $R_b$ at each occurrence is independently hydrogen, alkyl, alkenyl or haloalkyl;

wherein the aryl, heteroaryl, aryl moiety of the arylalkyl and the heteroaryl moiety of the heteroarylalkyl as represented by $R_a$ and $R_{a'}$ are independently unsubstituted or substituted with 1, 2, 3 or 4 substituents selected from the group consisting of alkyl, haloalkyl, alkenyl, hydroxy, alkoxy, —N(H)$_2$, —N(H)(alkyl), —N(alkyl)$_2$, —C(O)H, —C(O)alkyl, —C(O)OH, —C(O)O(alkyl), —C(O)NH$_2$, —C(O)N(H)(alkyl), —C(O)N(alkyl)$_2$, —CN and —NO$_2$, A is thiazolyl and is connected to $L_1$ and X through the carbon atoms in the ring; A is optionally further substituted with 1 or 2 substituents selected from the group consisting of alkyl, halogen, haloalkyl and hydroxyalkyl;

X is —C(H)=N—O—(CR$^y$R$^z$)$_p$—NR$_d$R$_e$, or —C(CR$^y$R$^z$)$_q$—NR$_d$R$_e$;

$R^y$ and $R^z$ at each occurrence are independently hydrogen, alkyl, haloalkyl or hydroxyalkyl;

p at each occurrence is independently 2 or 3;

q at each occurrence is independently 1, 2 or 3;

$R_d$ at each occurrence is independently hydrogen, alkyl, haloalkyl, —C(O)(alkyl), —C(O)N(H)$_2$, —C(O)N(H)(alkyl) or —C(O)N(alkyl)$_2$; and $R_e$ at each occurrence is independently hydrogen, alkyl or haloalkyl.

2. The compound of claim 1, wherein:
$A_2$ is C($R^1$);
$A_3$ is C(-$L_2$-$R^2$); and
$L_2$ is O.

3. The compound of claim 1, wherein $L_2$ is O and $R^2$ is alkyl.

4. The compound of claim 1, wherein $L_2$ is O, $R^2$ is alkyl and X is —C(H)=N(O)—(C$R^y R^z$)$_p$—N$R_d R_e$.

5. The compound of claim 1, wherein $L_2$ is O, $R^2$ is alkyl and X is —(C$R^y R^z$)$_q$—N$R_d R_e$.

6. The compound of claim 1 of formula (Ie)

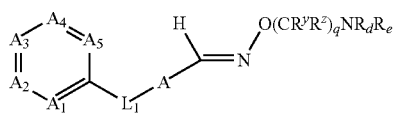

(Ie)

7. The compound of claim 1 selected from the group consisting of:
N-{(1S)-2-[({(1Z)-[2-(2-bromo-4-ethoxyphenoxy)-1,3-thiazol-5-yl]methylene}amino)oxy]-1-methylethyl}acetamide;
N-{(1S)-2-[({(1E)-[2-(2-bromo-4-ethoxyphenoxy)-1,3-thiazol-5-yl]methylene}amino)oxy]-1-methyl ethyl}propanamide;
N-{(1S)-2-[({(1E)-[2-(2-bromo-4-ethoxyphenoxy)-1,3-thiazol-5-yl]methylene}amino)oxy]-1-methyl ethyl}-N-methylurea; and
N-{(2E)-3-[2-(4-isopropoxyphenoxy)-1,3-thiazol-5-yl]-1-methylprop-2-enyl}acetamide;
or a pharmaceutically acceptable salt, prodrug, salt of a prodrug, or a combination thereof.

8. A method for treating metabolic syndrome in a mammal, comprising administering a compound of claim 1 having formula (I), or a pharmaceutically acceptable salt thereof.

9. A method for treating type II diabetes in a mammal comprising administering a compound of claim 1.

10. A method for treating obesity in a mammal comprising administering a compound of claim 1.

11. A pharmaceutical composition comprising a compound of claim 1 and a pharmaceutically acceptable carrier.

* * * * *